US008980610B2

(12) United States Patent
Selvitelli et al.

(10) Patent No.: US 8,980,610 B2
(45) Date of Patent: Mar. 17, 2015

(54) ARGININE INACTIVATION OF VIRUSES

(75) Inventors: Keith Selvitelli, Sutton, MA (US); Justin McCue, Belmont, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 594 days.

(21) Appl. No.: 13/130,540

(22) PCT Filed: Nov. 20, 2009

(86) PCT No.: PCT/US2009/006221
§ 371 (c)(1),
(2), (4) Date: Oct. 4, 2011

(87) PCT Pub. No.: WO2010/059232
PCT Pub. Date: May 27, 2010

(65) Prior Publication Data

US 2012/0015424 A1 Jan. 19, 2012

(51) Int. Cl.
*C12N 7/06* (2006.01)
*C12N 7/00* (2006.01)
*A61K 39/21* (2006.01)

(52) U.S. Cl.
CPC ........ *C12N 7/00* (2013.01); *C12N 2710/16763* (2013.01); *C12N 2740/13063* (2013.01)
USPC ..................... 435/238; 424/207.1; 424/208.1; 435/235.1

(58) Field of Classification Search
None
See application file for complete search history.

(56) References Cited

U.S. PATENT DOCUMENTS

| | | | |
|---|---|---|---|
| 5,116,950 | A | 5/1992 | Miyano et al. |
| 6,528,246 | B2 | 3/2003 | Stadler et al. |
| 6,955,917 | B2 | 10/2005 | Alred et al. |
| 7,348,004 | B2 | 3/2008 | Peters et al. |
| 7,381,408 | B2 | 6/2008 | Mezo et al. |
| 7,404,956 | B2 | 7/2008 | Peters et al. |
| 2005/0147618 | A1 | 7/2005 | Rivera et al. |

FOREIGN PATENT DOCUMENTS

| | | | |
|---|---|---|---|
| EP | 0 131 740 | B1 | 10/1990 |
| EP | 1144009 | * | 10/2002 |
| EP | 1 958 626 | A1 | 8/2008 |
| WO | WO 94/26287 | A1 | 11/1994 |
| WO | WO 00/40703 | A1 | 7/2000 |
| WO | WO 2007/008547 | A2 | 1/2007 |
| WO | WO 2008/086006 | A2 | 7/2008 |
| WO | WO 2009/140177 | A2 | 11/2009 |
| WO | WO 2010/005570 | A2 | 1/2010 |

OTHER PUBLICATIONS

Chu et al., 2001. Industrial choices for protein production by large-scale cell culture. Current Opinion in Biotechnology. 12: 180-187.*

Katsuyama et al. May 2008. Butyroyl-arginine as a potent virus inactivation agent. International Journal of Pharmaceutics.361 (2008) 92-98.*

Fan et al., Apr. 2008. Improving the refolding of NTA protein by urea gradient and arginine gradient size-exclusion chromatography. J. Biochem. Biophys. Methods 70 (2008). 1130-1138.*

Arakawa, T., et al., "Suppression of protein interactions by arginine: A proposed mechanism of the arginine effects," *Biophys. Chem. 127*(1-2):1-8, Elsevier Science B.V., Netherlands (2007).

Arakawa, T., et al., "The effects of arginine on protein binding and elution in hydrophobic interaction and ion—exchange chromatography," *Protein Expr. Purif. 54*(1):110-116, Elsevier Inc., United States (2007).

Arakawa, T., et al., "Synergistic virus inactivation effects of arginine," *Biotechnol. J. 4*(2):174-178, Wiley-VCH Verlag, Germany (2009).

Ejima, D., et al., "Effective elution of antibodies by arginine and arginine derivatives in affinity column chromatography," *Anal. Biochem. 345*(2):250-257, Academic Press, United States (2005).

Ishibashi, M., et al., "Is arginine a protein-denaturant?" *Protein Expr. Purif. 42*(1):1-6, Elsevier Inc., United States (2005).

Katsuyama, Y., et al,. "Butyroyl-arginine as a potent virus inactivation agent,"Database accession No. PREV200800640338, Biosis Biosciences Information Service, United States (Sep. 2008).

Kozloff, L. M., et al., "Critical Arginine Residue for Maintaining the Bacteriophage Tail Structure," *J. Virol. 3*(2):217-227, American Society for Microbiology, United States (1969).

Roberts P.L. et al., "Virus inactivation by protein denaturants used in affinity chromatography," Database accession No. PREV200800124234, Biosis Biosciences Information Service, United States (Oct. 2007).

Tsumoto, K., "Role of arginine in protein refolding, solubilization, and purification," *Biotechnol. Prog. 20*(5):1301-1308, American Institute of Chemical Engineers, United States (2004).

Utsunomiya, H., et al., "Co-operative thermal inactivation of herpes simplex virus and influenza virus by arginine and NaCl," *Int. J. Pharm. 366*(1-2):99-102, Elsevier Science B.V., Netherlands (2009).

Yamasaki, H., et al., "Arginine Facilities Inactivation of Enveloped Viruses,"*J. Pharm. Sci. 97*(8):3067-3073, Wiley-Liss, Inc. and the American Pharmacists Association, United States (2008).

International Conference on Harmonisation; Guidance on Viral Safety Evaluation of Biotechnology Products Derived from Cell Lines of Human or Animal Origin, 63 Fed. Reg. 51074-51084 (Sep. 24, 1998).

Points to Consider in the Manufacture and Testing of Monoclonal Antibody Products for Human Use, U.S. Department of Health and Human Services, FDA, and Center for Biologics Evaluation and Research, Feb. 28, 1997.

(Continued)

*Primary Examiner* — Benjamin P Blumel
(74) *Attorney, Agent, or Firm* — Sterne Kessler Goldstein & Fox P.L.L.C.

(57) ABSTRACT

The present invention pertains to methods of using arginine to inactivate or reduce the infectious titer of enveloped viruses potentially present in biological compositions produced by eukaryotic cells (such as a antibodies or other therapeutic proteins). In some embodiments, inactivation or reduction of viral titers by exposure to arginine is achieved in a neutral (pH ~7) or near neutral (~pH 6 to ~pH 8) environment.

35 Claims, 17 Drawing Sheets

(56) References Cited

OTHER PUBLICATIONS

International Search Report for International Application No. PCT/US2009/06221, completed Feb. 19, 2010.
Yamasaki, H., et al., Effect of Arginine on Temperature of Thermal Inactivation of Virus, 56th Annual Meeting of the Japanese Society for Virology, Program/Abstracts from Oct. 26-28, 2008, p. 383.
English language translation of Yamasaki, H., et al., Effect of Arginine on Temperature of Thermal Inactivation of Virus, 56th Annual Meeting of the Japanese Society for Virology, Program/Abstracts from Oct. 26-28, 2008, p. 383.
Yamasaki, H., et al., slides from the 56th Annual Meeting of the Japanese Society for Virology, Oct. 26-28, 2008, with select English language translations.
Third Party Observations pursuant to Article 115 EPC, European Patent Application No. 09761053.9, European Patent Office, Netherlands, dated Sep. 25, 2013.
English language translation of Third Party Observations for Japanese Patent Application No. 2011-537425, Japanese Patent Office, Japan, mailed Sep. 11, 2013.
Third Party Observations for Japanese Patent Application No. 2011-537425, Japanese Patent Office, Japan, mailed Sep. 11, 2013.

* cited by examiner

ARGININE INACTIVATION OF VIRUSES

CROSS-REFERENCE TO RELATED APPLICATIONS

This application is the National Stage of International Application Number PCT/US2009/006221, filed Nov. 20, 2009, which claims the benefit of U.S. Provisional Application Ser. No. 61/116,534, filed Nov. 20, 2008, which is incorporated by reference herein.

FIELD OF THE INVENTION

The present invention relates to inactivation of viruses or reduction of infectious virus titers. More specifically, the invention relates to inactivation or reduction of infectious virus titers by treatment with arginine or salts thereof. The invention also relates to inactivation or reduction of infectious virus titers as a component of therapeutic product preparation and purification regimens.

BACKGROUND

The advent of recombinant DNA technology has opened the door for many protein-based biological therapies. In most circumstances, these protein therapeutics are produced by cells, highly purified, and prepared for administration to patients. Often, the recombinant DNA encoding the therapeutic protein, must be transfected into the protein-producing cells. Viruses can remain in the culture after transfection and contaminate the protein samples. Additionally, cells used for expressing proteins of interest may encode viral genomes in their DNA or otherwise contain endogenous viruses, which is another potential source of contamination to a therapeutic product derived from cells. Therefore, biologically-derived therapeutics must undergo at least two robust virus purification steps in order to meet the safety requirements of regulatory agencies such as the FDA to ensure no active viruses are administered to a patient.

There are several methods known in the art to inactivate viruses. Treatment with low pH, the use of detergents, salts, and heat inactivation have all been used to inactivate viruses in protein preparations, but each method has its own disadvantages, and may not be suitable or optimal for some protein products as discussed in further detail below.

Low pH has been used to inactivate viruses as in U.S. Pat. No. 6,955,917, but this has the potential to precipitate proteins, cause aggregation of the product, and/or alter the conformation of certain proteins which can lead to product loss.

EP0131740 B1 describes a method for the inactivation of lipid-coated viruses in compositions containing labile proteins. The method described in EP 0131740 B1 consists of contacting the composition containing labile protein with an effective amount of a dialkyl or trialkyl phosphate for a period of time sufficient to render the composition containing labile protein free of lipid-containing viruses.

U.S. Pat. No. 6,528,246 B2 describes a method for inactivation of viruses using combinations of tri-n-butyl phosphate and Tween, or sodium cholate/TNBP (tri-n-butyl phosphate) and other buffers, detergents and/or surfactants, but requires the use of high concentrations of auxiliary agents such as saccharose and also heat inactivation in the range of 55° C. to 67° C. which can denature certain proteins and lead to degradation resulting in loss of product.

Other detergents such as TRITON® X-100 (Sigma-Aldrich Corp., St. Louis, Mo., USA) have been used to inactivate viruses, but present problems with high amounts of waste product when used on an industrial scale. In the examples of WO 94/26287, a "detergent/salting-out" method is applied to three isolated proteins in solution, which are transferrin, antithrombin III and albumin. If the TRITON® X-100 method is applied under conditions such that the yield of the target protein is not substantially affected, frequently the concentration of TRITON® in the product is still very high. In example 4 of WO 94/26287, the inventors recovered 95% of albumin, but obtained a product comprising 250 ppm TRITON® X-100 and 35 ppm TNBP. Especially when producing medical preparations, TRITON® X-100 concentrations above 50 ppm, or even above 10 ppm are preferably avoided, and it is generally desirable to reduce the detergent content as much as possible. Additionally, some therapeutic proteins are inactivated by TRITON® X-100 and, thus, this method for virus inactivation is not optimal for many protein products.

Accordingly, there is a need in the art to inexpensively and safely inactivate or reduce infectious virus titers while preserving the integrity, biological, and/or therapeutic activity of the protein product.

Arginine is unique among naturally occurring amino acids in that it has been found to prevent protein aggregation and suppress protein interactions without substantially altering protein conformation. Given these attributes, 0.1M to 1M arginine has been used to facilitate refolding of recombinant proteins solubilized from inclusion bodies and 0.5 to 2M arginine has been used to extract active, folded proteins from insoluble pelleted material expressed as a recombinant product in *E. coli*. (Tsumoto et al., *Biotechnology.,* 20, 1301-1308 (2004); Ishibashi et al., *Protein Expression and Purification,* 42, 1-6 (2005); Arakawa et al., *Biophysical Chemistry,* 127, 1-8 (2008)). Arginine has also been used to enhance recovery of proteins from various types of chromatographic media such as in Protein-A, gel permeation, and dye-affinity chromatography. (Arakawa et al., *Protein Expression and Purification,* 54, 110-116 (2007); Ejima et al., *Analytical Biochemistry,* 345, 250-257 (2005)). Arginine has also been used as one component in protein stabilizing formulations, for example, to protect proteins from being inactivated during heat treatment procedures. (Miyano, et al., U.S. Pat. No. 5,116,950, issued May 26, 1992).

Kozloff et al. have observed that use of 0.2M arginine irreversibly inactivated preparations of some T-even strains of bacteriophage (T2L, a non-enveloped virus). Kozloff et al. also found that this virus specific inactivation was most effective at 30° C. and in a pH range of 6.5 to 8.25, and could be accomplished with arginine at 0.033 to 0.2M. However, arginine inactivation of T2L was increasingly ineffective at concentrations of above 0.4 M. Kozloff et al. also observed that arginine did not inactivate T-odd strains of bacteriophage. This difference is presumably due to differences in tail structures of T-even versus T-odd bacteriophage (with which arginine apparently specifically interacts to bring about T-even inactivation). Kozloff et al., Jour. Virol., 3(2), 217-227 (1969).

Yamasaki et al. have observed that at a low (acidic) pH and at low temperatures (samples on ice), arginine can inactivate the enveloped herpes simplex virus type-1 (HSV-1) and influenza virus. However, at more neutral pH levels (i.e., pH 5.0-pH 7.0), Yamasaki et al. found arginine to be ineffective at inactivating these viruses. Yamasaki et al. also found that arginine was ineffective at inactivating non-enveloped polio virus. (Yamaski et al., *Journal of Pharmaceutical Sciences*, (Jan. 10, 2008) 97(8), 3067-3073).

BRIEF DESCRIPTION OF THE INVENTION

The present invention allows the use of high concentrations of arginine to effectively inactivate or reduce infectious titers of lipid coated (enveloped) viruses that may be present during the production of a biological product, such as a monoclonal antibody or other therapeutic protein.

In one embodiment, virus inactivation or reduction of infectious virus titers occurs in a neutral (pH ~7) environment.

In other embodiments virus inactivation or reduction of infectious virus titers occurs at temperatures ranging from 2° to 42° C.

In one embodiment, the present invention provides a component in a process of obtaining a protein preparation purified to a degree suitable for administration, preferably as therapeutically useful compound, to a living subject. For example, but without limitation, the present invention may be used as part of the process in preparing therapeutically useful proteins such as factor VIII, factor IX, fibrinogen, gamma-globulin, antibodies and antibody fragments. Also, for example, but without limitation, the present invention may be used to inactivate or reduce infectious virus titers of enveloped viruses such as a mammalian or avian Leukemia virus, Herpes virus, Pox virus, Hepadnavirus, Flavivirus, Togavirus, Coronavirus, Hepatitis virus, Retrovirus, Orthomyxovirus, Paramyxovirus, Rhadovirus, Bunyavirus, Filovirus, and Reovirus.

DETAILED DESCRIPTION OF THE INVENTION

Definitions

Figure 1:
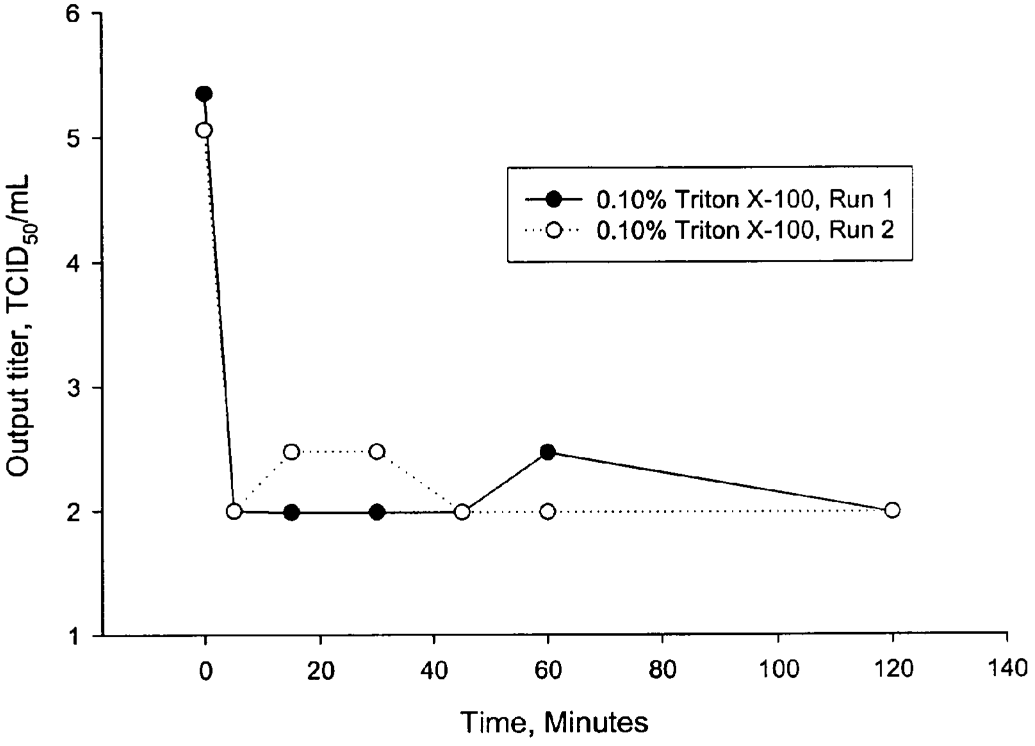
FIG. 1 depicts the kinetics of X-MLV inactivation by 0.10% TRITON® X-100.

Terms are used in the present specification and claims as generally used and understood in the related art unless explicitly defined or stated otherwise herein. In the case where there are two or more definitions of a term which is used and/or accepted within the art, the definition of the term as used herein is intended to include all such meanings unless explicitly stated to the contrary.

As used herein, the term "wash solution" refers to the solution used to separate contaminant(s), such as process-related impurities, from a target protein and a stationary phase culture such as a Size Exclusion Chromatography (SEC), Ion Exchange Chromatography (IEC), affinity chromatography or other chromatographic medium. In addition to a salt, the wash solution may comprise a buffer, a detergent, a solvent, a polymer, or any combination thereof. In some embodiments, the wash solution may comprise about 0.1M, 0.2 M, 0.3 M, 0.4 M, 0.5 M, 0.6 M, 0.7 M, 0.8 M, 0.9 M, 1 M, 1.1 M, 1.2 M, 1.3 M, 1.4 M, 1.5 M, 1.6 M, 1.7 M, 1.8 M, 1.9 M, 2 M, 2.5 M, or 3.0 M arginine or salt thereof.

The term "buffer" refers to a solution that resists changes in pH by the action of its acid-base conjugate components.

The term "elution reagent" refers to a reagent used to elute or dissociate a therapeutic protein from a stationary phase culture such as an SEC, IEC, affinity or other chromatographic medium. In addition to arginine, the elution reagent may comprise a buffer, a salt, a detergent, a solvent, a polymer, a glycol compound or any combination thereof.

Examples of "glycols" useful in the methods of the invention include, without limitation, ethylene glycol, propylene glycol, hexylene glycol, polyethylene glycol, or polypropylene glycol.

As used herein, the term "process-related impurities" refers to any undesirable component in a biological preparation such as viruses, nucleotides, polynucleotides, non-target proteins (such as host cell proteins, HCP), other cellular components (such as lipids and glycolipids), and any other contaminants that arise from, or during, production, separation, and/or purification processes.

The term "recombinantly produced," when used in reference to a protein, refers to that protein produced using recombinant DNA technology. In some embodiments, the recombinantly produced protein is produced by a mammalian cell. In some embodiments, the cell is a human cell. In other embodiments, the cell is a non-human cell such as Chinese Hamster Ovary (CHO) cell or Baby Hamster Kidney (BHK) cell. The cell type can be any suitable cell for producing recombinant proteins according to methods of the invention.

As used herein, the term "fusion protein," when used in reference to polypeptides such as an "Fc fusion" protein, refers to polypeptides comprising amino acid sequences derived from two or more heterologous polypeptides, such as portions of proteins which are encoded by separate genes (whether the genes occur in the same or in a different species of organism), or wherein a fusion protein refers to a polypeptide comprising a portion of a naturally occurring gene (or a derivative or variant thereof) covalently linked with an artificial or non-naturally occurring peptide or polypeptide.

As used herein, the term "inactivate" or other forms of this word (e.g., inactivation, inactivated, inactivates, etc.) when used in reference to viruses is intended to indicate not only complete virus inactivation (i.e., no detectable infectious virus) but also the detectable reducing or reduction of infectious virus titers (i.e., lowering or lowered levels of detectable infectious virus). Thus, the reducing or reduction of infectious virus titers is included within the meaning of "virus inactivation" (and other forms of this term) whether or not such reducing or reduction is explicitly stated herein.

"Therapeutic protein" preparations may include recombinant or non-recombinant proteins. Examples of non-recombinant proteins include proteins isolated from whole blood, blood plasma, plasma concentrate, precipitates from any fraction of blood plasma, supernatant from any fractioning of blood plasma, serum, cryoprecipitates, cell lysates, or similar sources.

Therapeutic proteins prepared according to the present invention includes any therapeutically useful peptide, polypeptide, glycopeptide, or protein.

The term "Fc region" refers to a C-terminal region of an IgG heavy chain. In a particular embodiment, the Fc region refers to the C-terminal region of a human IgG heavy chain. Although the boundaries of the Fc region of an IgG heavy chain might vary slightly, the human IgG heavy chain Fc region is usually defined to span from the amino acid residue at position $Cys^{226}$ of the native polypeptide to the carboxyl-terminus.

As used herein, the term "mass concentration," when used in reference to the removal of process-related impurities, refers to a ratio of the mass of process-related impurities to the mass of therapeutic protein. For example, the ratio may be calculated as nanograms of process-related impurities per milligram of therapeutic protein when the mass concentration is parts per million (ppm), and the ratio may be calculated as picograms of process-related impurities per milligram of therapeutic protein when the mass concentration is parts per billion (ppb).

As used herein, the terms "percent recovery" and "percent purity," are intended to mean the recovery or purity achieved when a target compound (e.g., a protein) is conveyed through a purification step or procedure, compared to the quantity or purity of the target compound in the sample prior to the purification step or procedure. Achieving an increase in percent purity entails obtaining a product with reduced levels of contaminants (in proportion to the target compound) when a sample is compared before and after a purification step or procedure. Preferred percentages within the meaning of percent recovery and percent purity as defined above include, without limitation, at least about 50%, at least about 60%, at least about 70%, at least about 80%, at least about 90%, at least about 95%, at least about 98%, and at least about 99%.

It is to be noted that the terms "a" or "an" refer to both singular and plural forms of the terms; for example, "a therapeutic protein," is understood to represent one or more therapeutic proteins. As such, the terms "a" (or "an"), "one or more," and "at least one" can be used interchangeably herein.

In some embodiments, the present invention provides methods of inactivating a virus comprising contacting the virus with a solution comprising at least about 0.2 M arginine, wherein the solution is at a pH above about 5.0 and wherein the virus is not a bacteriophage or other non-enveloped virus.

In some embodiments, the present invention relates to a method of reducing the titer of infectious virus in a therapeutic protein preparation comprising exposing the therapeutic protein preparation to a solution having a final concentration of at least about 0.2M arginine and a pH above about 5.0 and wherein the virus is not a bacteriophage or other non-enveloped virus.

In some embodiments, the therapeutic protein is a recombinant protein. In other embodiments, the recombinant protein may be an immunoglobulin (antibody) or fragment thereof. In yet other embodiments the protein preparation may comprise a blood coagulation factor.

The blood coagulation factor of the present invention can be a blood coagulation factor such as, but without limitation, Factor-I (fibrinogen), Factor-II (prothrombin), Tissue factor, Factor-V (proaccelerin, labile factor), Factor-VI, Factor-VII (stable factor), Factor-VIII (antihemophilic factor), Factor-IX (Christmas factor), Factor-X (Stuart-Prower factor), Factor-XI (plasma thromboplastin antecedent), Factor-XII (Hageman factor), Factor-XIII (fibrin-stabilizing factor), von Willebrand factor, prekallikrein, high molecular weight kininogen (HMWK), fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI1), and plasminogen activator inhibitor-2 (PAI2).

In some embodiments, therapeutic proteins prepared by methods of the present invention are produced by eukaryotic cells. In some embodiments, the eukaryotic cells of the invention are mammalian cells. In other embodiments, the mammalian cells are Chinese Hamster Ovary (CHO) cells or Baby Hamster Kidney (BHK) cells. In yet other embodiments, the mammalian cells are human cells. In other embodiments the cells are multi-hybrid (2 or more cells) fused together (e.g., mouse or human hybridoma cells).

The arginine viral inactivation method of the present invention may be performed prior to any purification procedure (for example, a chromatographic procedure), during or between one or more purification procedures, and/or after all purification procedures.

In some embodiments, the invention comprises proteins produced by methods of the present invention.

The chromatography steps of the present invention may employ any type of chromatographic method. For example, such methods include without limitation: Such chromatography methods include, for example but without limitation: gas chromatography, liquid chromatography (e.g., high performance liquid chromatography); affinity chromatography (such as Protein-A or antibody-antigen affinity chromatography); supercritical fluid chromatography; ion exchange chromatography (such as anion or cation exchange chromatography); size-exclusion chromatography; reversed phase chromatography; two-dimensional chromatography; simulated moving bed chromatography, pyrolysis gas chromatography, fast protein (FPLC) chromatography; countercurrent chromatography; chiral chromatography; aqueous normal phase (ANP) chromatography; mixed mode chromatography; and, pseudo-affinity chromatography.

The pH range used in the arginine inactivation steps of the present invention can be above or about 5.0, above or about 5.5, above or about 6.0, above or about 6.5, above or about 7.0, above or about 8.0, above or about 9.0. In some embodiments the arginine inactivation step is carried out at a pH range from about 5.0 to about 9.0. In other embodiments the pH range is from about 6.0 to about 8.5. In other embodiments, the pH range is about 6.5 to about 7.5. In some embodiments, the pH is about 7.0.

In some embodiments, the arginine concentration is about 0.1M, 0.2M, 0.3M, 0.4M, 0.5 M, 0.6M, 0.7M, 0.8M, 0.9M, 1

M, 1.5 M, 2 M, 2.5M, or about 3 M. In some embodiments, the viral inactivation methods of the present invention take place at an arginine concentration of about 0.2 M to about 3 M. In some embodiments, the arginine concentration is within a range of about 0.5 M to about 3 M. In other embodiments, the arginine concentration is within a range of about 1 M to about 3 M. In yet other embodiments, the arginine concentration is within a range of about 1 M to about 2 M.

It is to be understood that "arginine" as used herein refers to arginine and salts thereof.

In some embodiments virus inactivation via use of arginine is carried out at temperatures of about 0° C. to about 55° C.; including for example temperature ranges of about 0° C. to about 4° C., about 0° C. to 8° C., about 0° C. to about 12° C., about 0° C. to about 18° C., about 0° C. to about 20° C., about 0° C. to about 25° C., about 0° C. to about 37° C., about 0° C. to about 40° C., about 0° C. to about 42° C., about 2° C. to about 4° C., about 2° C. to about 8° C., about 2° C. to about 12° C., about 2° C. to about 18° C., about 2° C. to about 20° C., about 2° C. to about 25° C., about 2° C. to about 37° C., about 2° C. to about 40° C., about 2° C. to about 42° C., about 2° C. to about 55° C., about 4° C. to about 8° C., about 4° C. to about 12° C., about 4° C. to about 18° C., about 4° C. to about 20° C., about 4° C. to about 25° C., about 4° C. to about 37° C., about 4° C. to about 40° C., about 4° C. to about 42° C., about 4° C. to about 55° C., about 8° C. to about 12° C., about 8° C. to about 18° C., about 8° C. to about 20° C., about 8° C. to about 25° C., about 8° C. to about 37+ C., about 8° C. to about 40° C., about 8° C. to about 42° C., about 8° C. to about 55° C., about 12° C. to about 18° C., about 12° C. to about 20° C., about 12° C. to about 25° C., about 12° C. to about 37° C., about 12° C. to about 40° C., about 12° C. to about 42° C., about 12° C. to about 55° C., about 18° C. to about 20° C., about 18° C. to about 25° C., about 18° C. to about 37° C., about 18° C. to about 40° C., about 18° C. to about 42° C., about 18° C. to about 55° C., about 20° C. to about 25° C., about 20° C. to about 37° C., about 20° C. to about 40° C., about 20° C. to about 42° C., about 20° C. to about 55° C., about 25° C. to about 37° C., about 25° C. to about 40° C., about 25° C. to about 42° C., about 25° C. to about 55° C., about 37° C. to about 40° C., about 37° C. to about 42° C., about 37° C. to about 55° C., about 40° C. to about 42° C., about 40° C. to about 55° C., and about 42° C. to about 55° C.

In some embodiments virus inactivation via use of arginine is carried out at temperatures of 0° C. to 55° C.; including for example temperature ranges of 0 to 4° C., 0 to 8° C., 0 to 12° C., 0 to 18° C., 0 to 20° C., 0 to 25° C., 0 to 37° C., 0 to 40° C., 0 to 42° C., 2 to 4° C., 2 to 8° C., 2 to 12° C., 2 to 18° C., 2 to 20° C., 2 to 25° C., 2 to 37° C., 2 to 40° C., 2 to 42° C., 2 to 55° C., 4 to 8° C., 4 to 12° C., 4 to 18° C., 4 to 20° C., 4 to 25° C., 4 to 37° C., 4 to 40° C., 4 to 42° C., 4 to 55° C., 8 to 12° C., 8 to 18° C., 8 to 20° C., 8 to 25° C., 8 to 37° C., 8 to 40° C., 8 to 42° C., 8 to 55° C., 12 to 18° C., 12 to 20° C., 12 to 25° C., 12 to 37° C., 12 to 40° C., 12 to 55° C., 18 to 20° C., 18 to 25° C., 18 to 37° C., 18 to 40° C., 18 to 42° C., 18 to 55° C., 20 to 25° C., 20 to 37° C., 20 to 40° C., 20 to 42° C., 20 to 55° C., 25 to 37° C., 25 to 40° C., 25 to 42° C., 25 to 55° C., 37 to 40° C., 37 to 42° C., 37 to 55° C., 40 to 42° C., 40 to 55° C., and 42 to 55° C.

The present invention includes inactivation of viruses as a component of a therapeutic product (or drug substance) preparation regimen wherein virus inactivation is accomplished by contacting a therapeutic product, or composition containing a therapeutic product, with arginine. In one embodiment virus is contacted in a solution with a final arginine concentration of about 0.1M or greater. In certain embodiments the final arginine concentration is about 0.5M or greater or about 1.0M or greater. In certain embodiments virus inactivation is accomplished in a solution with arginine wherein the solution is at a pH value which is neutral (about pH 7) or near neutral (about pH 6 to about pH 8.5). In certain embodiments the neutral or near neutral pH value is about 6.0, about 6.5, about 7.0, about 7.5, about 8.0, and about 8.5. In one embodiment virus inactivation with arginine is performed before any prior therapeutic product purification steps or procedures. In one embodiment virus inactivation is performed as part of a cell culture harvest procedure. In one embodiment virus inactivation is performed after a cell culture harvest procedure. In one embodiment virus inactivation is performed as part of a cell culture supernatant clarification procedure. In one embodiment virus inactivation is performed after a cell culture supernatant clarification procedure. In one embodiment virus inactivation is performed during (as part of), or in between, therapeutic product purification steps or procedures. In one embodiment virus inactivation is performed after one or more therapeutic product purification steps or procedures. In one embodiment virus inactivation is performed after one or more therapeutic product purification steps comprising use of chromatography. In one embodiment virus inactivation is performed after one or more therapeutic product purification steps comprising use of affinity chromatography, such as Protein-A or Protein-G chromatography (or chromatography with Protein-A or Protein-G derivatives or analogs). In one embodiment virus inactivation is performed between chromatography purification steps or procedures. In one embodiment virus inactivation is performed prior to a virus filtration step or procedure. In one embodiment virus inactivation is performed after a virus filtration step or procedure. In one embodiment virus inactivation is performed after a chromatography purification step or procedure and before a virus filtration step or procedure. In one embodiment virus inactivation is performed prior to an ultrafiltration or diafiltration step or procedure. In one embodiment virus inactivation is performed after an ultrafiltration or diafiltration step or procedure. In one embodiment virus inactivation is performed after a virus filtration step or procedure and prior to an ultrafiltration or diafiltration step or procedure. In one embodiment virus inactivation is performed after all therapeutic product purification steps or procedures and prior to final therapeutic product formulation. In one embodiment virus inactivation is performed as part of a final therapeutic product formulation process.

The methods of the present invention are useful for inactivating a wide range of enveloped viruses. Viruses that may be inactivated by embodiments of the present invention include, without limitation, enveloped viruses classified such as, for example, mammalian or avian Leukemia viruses, Herpes viruses, Pox viruses, Hepadnaviruses, Flaviviruses, Togaviruses, Coronaviruses, Hepatitis viruses, Retroviruses, Orthomyxoviruses, Paramyxoviruses, Rhadoviruses, Bunyaviruses, Filoviruses, and Reoviruses. The terms "virus(es)" and "viral particle(s)" may be used interchangeably herein.

EXAMPLES

Data below demonstrate inactivation of various enveloped viruses by exposure to arginine. For purposes of comparison, data below also show virus inactivation by exposure to low pH and the detergent TRITON® X-100 (Sigma-Aldrich Corp., St. Louis, Mo., USA). Also for comparison, data below show virus non-activation by exposure to high concentrations of the amino acid glycine. Exemplary viruses tested include:

a) Xenotropic Murine leukemia virus (X-MLV), a model endogenous retrovirus (enveloped, RNA genome virus) potentially present in cell culture harvests of Chinese Hamster Ovary cells (CHO) (a cell line commonly used to produce recombinant proteins);
b) Murine minute virus (MMV) as a model adventitious virus (non-enveloped, DNA genome) potentially introduced during protein production/processing; and
c) Suid herpesvirus 1 (SuHV-1) as a model enveloped, DNA containing virus with moderate resistance to physical/chemical inactivation. See, Table 15.

Example 1

TRITON® X-100, Low pH, and Arginine Inactivation of X-MLV in Preparation Samples of Recombinant Antibody GE2-Fcγ-Fcϵ

Virus inactivation kinetics obtained by exposure to low pH, TRITON® X-100 and arginine were studied using sample process intermediates of a recombinant antibody designated GE2-Fcγ-Fcϵ. The process intermediates used in these inactivation studies are shown in Table 1. All studies were performed at 2-8° C.

For the TRITON® X-100 inactivation studies, TRITON® X-100 was added to the GE2-Fcγ-Fcϵ clarified conditioned media (CCM) at concentrations of 0.10% (v/v) and 0.20% (v/v). MABSELECT™ (GE Healthcare Bio-Sciences Corp., Piscataway, N.J., USA) Protein-A chromatography eluates containing GE2-Fcγ-Fcϵ with the pH adjusted to 3.7 or 3.9 were used as the starting material for the low pH viral inactivation studies. Neutralized MABSELECT™ Eluate buffer (1.0 M arginine-HCl, ~5 mM Tris, pH 7.3 (+/−) 0.5) and neutralized MABSELECT™ Eluate buffer containing GE2-Fcγ-Fcϵ were also used as process intermediates for the additional inactivation studies. The process intermediates used in these studies were known to be stable under the examined conditions.

TABLE 1

Process Intermediates Used in GE2-Fcγ-Fcϵ X-MLV Inactivation Studies

| Study | Process Intermediate | GE2-Fcγ-Fcϵ (mg/mL) |
|---|---|---|
| TRITON ® X-100 Inactivation | Clarified conditioned media | 1.14[a] |
| Low pH Inactivation | MABSELECT ™ Eluate | 4.7[b] |
| Arginine Inactivation (neutral pH) | MABSELECT ™ Eluate (neutralized) | 3.3[b] |

[a]Concentration determined from Protein G HPLC titer assay
[b]Concentration determined from Absorbance (280 nm)

A) TRITON® X-100 X-MLV Inactivation Experiments

TRITON® X-100 inactivation experiments were performed in duplicate using final concentrations of 0.10% or 0.20% (v/v) TRITON® X-100 in GE2-Fcγ-Fcϵ clarified conditioned media. Table 2 shows parameters in four experiments performed in these studies.

TABLE 2

Parameters in TRITON ® X-100 Inactivation Studies

| Experiment No. | % TRITON ® X-100 (v/v) | GE2-Fcγ-Fcϵ Concentration (mg/mL) |
|---|---|---|
| 1 | 0.10 | 1.13 |
| 2 | 0.10 | 1.13 |
| 3 | 0.20 | 1.12 |
| 4 | 0.20 | 1.12 |

Figure 2:
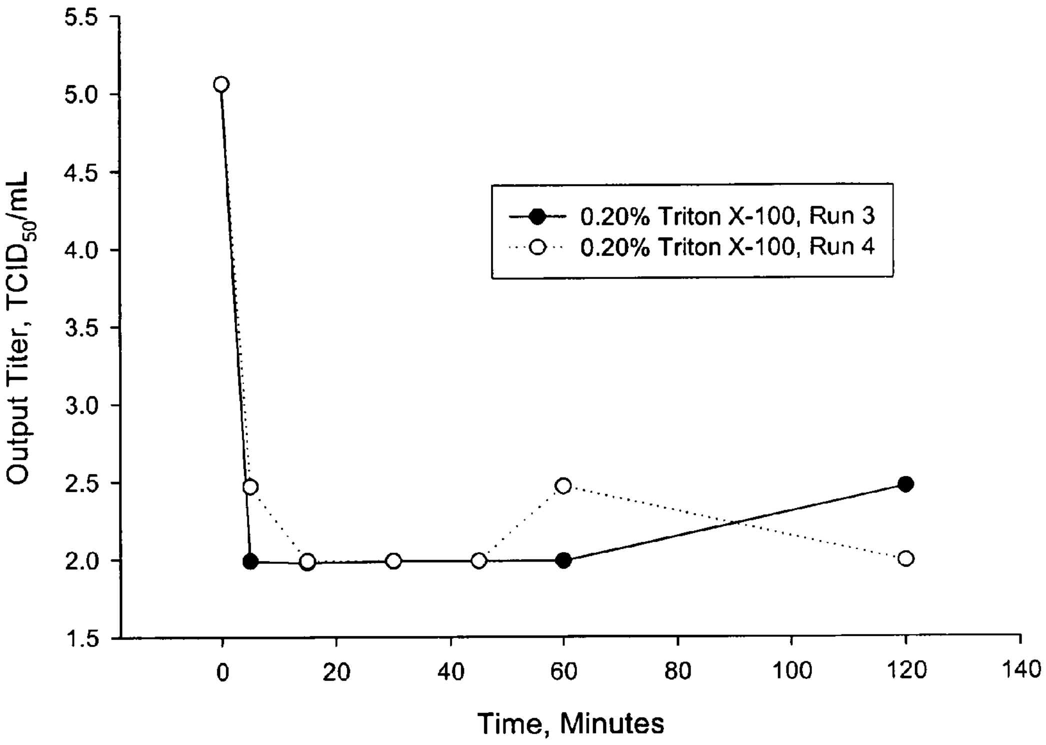
FIG. 2 depicts the kinetics of X-MLV inactivation by 0.20% TRITON® X-100.

A summary of the virus clearance results for the TRITON® X-100 inactivation studies are shown in Tables 3 and 4. Tables 3 and 4 summarize X-MLV Reduction Factors (RF) at various time points, while Table 13 summarizes the RF values for the four runs after 120 min exposure to TRITON® X-100. FIGS. 1 and 2 show the X-MLV titer as a function of time for 0.10% and 0.20% TRITON® X-100 addition, respectively.

In both 0.10% and 0.20% TRITON® X-100 inactivation studies, X-MLV was below detection limits after 5 minutes of detergent exposure; indicating rapid inactivation of X-MLV (FIGS. 1 and 2). Reduction factors of ≥3.1 and ≥2.6 for X-MLV were achieved by addition of 0.10% and 0.20% (v/v) TRITON® X-100, respectively, to the GE2-Fcγ-Fcϵ clarified conditioned media. Results of these studies showed that TRITON® X-100 could be used at concentrations of ≥0.10% to effectively inactivate X-MLV in GE2-Fcγ-Fcϵ MABSELECT™ process samples.

TABLE 3

X-MLV inactivation data for GE2-Fcγ-Fcϵ samples exposed to 0.10% TRITON ® X-100.

| Sample ID/ Description | Titer of quenched sample, $Log_{10}$ $TCID_{50}$/mL[a] | Dilution factor from quench[b] | Adjusted titer of sample, $Log_{10}$ $TCID_{50}$/mL[c] | RF[d] |
|---|---|---|---|---|
| Positive Virus Control | 5.23 | N/A[e] | 5.23 | N/A |
| Virolog Run #1 | | | | |
| Load Control (Time = 0 min.) | 5.35 | N/A | 5.35 | N/A |
| Hold Control | 3.80 | 20 | 5.10 | 0.3 |
| Time = 5 min. | ≤0.70 | 20 | ≤2.00 | ≥3.4 |
| Time = 15 min. | ≤0.69 | 20 | ≤1.99 | ≥3.4 |
| Time = 30 min. | ≤0.69 | 20 | ≤1.99 | ≥3.4 |
| Time = 45 min. | ≤0.69 | 20 | ≤1.99 | ≥3.4 |
| Time = 60 min. | ≤1.17 | 20 | ≤2.47 | ≥2.9 |
| Time = 120 min. | ≤0.69 | 20 | ≤1.99 | ≥3.4 |
| Virology Run #2 | | | | |
| Positive Virus Control | 5.35 | N/A[e] | 5.35 | N/A |
| Load Control (T0) | 5.06 | N/A | 5.06 | N/A |
| Hold Control | 3.86 | 20 | 5.16 | −0.1 |
| Time = 5 min. | ≤0.70 | 20 | ≤2.00 | ≥3.1 |

TABLE 3-continued

X-MLV inactivation data for GE2-Fcγ-Fcε samples exposed to 0.10% TRITON ® X-100.

| Sample ID/ Description | Titer of quenched sample, $Log_{10}$ $TCID_{50}$/mL[a] | Dilution factor from quench[b] | Adjusted titer of sample, $Log_{10}$ $TCID_{50}$/mL[c] | RF[d] |
|---|---|---|---|---|
| Time = 15 min. | ≤1.18 | 20 | ≤2.48 | ≥2.6 |
| Time = 30 min. | ≤1.18 | 20 | ≤2.48 | ≥2.6 |
| Time = 45 min. | ≤0.69 | 20 | ≤1.99 | ≥3.1 |
| Time = 60 min. | ≤0.69 | 20 | ≤1.99 | ≥3.1 |
| Time = 120 min. | ≤0.69 | 20 | ≤1.99 | ≥3.1 |

[a]Titer obtained from $TCID_{50}$ assay.

[b]Dilution factor = 20 (from quenching* 1 mL of spiked TA*** with 19 mL of media).

[c]Titer of sample, adjusted for the dilution factor. Obtained by multiplying titer from $TCID_{50}$ assay and the dilution factor from the quench.

$$RF = \log_{10}\frac{(\text{Input virus titer per mL})\times\text{Input volume}}{(\text{Output virus titer per mL})\times\text{Output volume}}$$

Note:

Input volume = output volume. Final quenched volume of each sample was 20 ml.

[e]Not applicable.

*A "Hold Control" is a sample that is not exposed to the virus inactivation process, and represents what the virus level would be if an inactivation process was not used. The "Hold Control" sample is held for the same time and temperature as the test article. Thus, any loss in virus titer measured in the hold control (which is not expected) would be due to events other than the inactivation process.

**Quenching indicates dilution or changing virus inactivation sample conditions into non-inactivation conditions. For example, quenching Tween inactivation conditions is done by diluting a sample containing Tween to a Tween concentration less than the critical level required for micelle formation, thereby nullifying the ability of Tween to inactivate virus. Similarly, low pH virus inactivation conditions are quenched by increasing the pH to neutral or near neutral levels.

***"TA" (Test Article) is the protein solution which is being evaluated for Virus inactivation. A "Spiked" Test Article is one in which virus has been added ("spiked into") to the solution.

TABLE 4

X-MLV inactivation data for GE2-Fcγ-Fcε samples exposed to 0.20% TRITON ® X-100

| Sample ID/Description | Titer of quenched sample, $Log_{10}$) $TCID_{50}$/mL[a] | Dilution factor from quench[b] | Adjusted titer of sample, $Log_{10}$ $TCID_{50}$/mL[c] | RF[d] |
|---|---|---|---|---|
| Virus Control | 5.29 | N/A[e] | 5.29 | N/A |
| Virology Run #3 | | | | |
| Load Control (T0) | 5.06 | N/A | 5.06 | N/A |
| Hold Control | 3.97 | 20 | 5.27 | −0.2 |
| Time = 5 min. | ≤0.69 | 20 | ≤1.99 | ≥3.1 |
| Time = 15 min. | ≤0.68 | 20 | ≤1.98 | ≥3.1 |
| Time = 30 min. | ≤0.69 | 20 | ≤1.99 | ≥3.1 |
| Time = 45 min. | ≤0.69 | 20 | ≤1.99 | ≥3.1 |
| Time = 60 min. | ≤0.69 | 20 | ≤1.99 | ≥3.1 |
| Time = 120 | ≤1.17 | 20 | ≤2.47 | ≥2.6 |
| Virology Run #4 | | | | |
| Virus Control | 5.29 | N/A[e] | 5.29 | N/A |
| Load Control (T0) | 5.06 | N/A | 5.06 | N/A |
| Hold Control | 3.86 | 20 | 5.16 | −0.1 |
| Time = 5 min. | ≤1.17 | 20 | ≤2.47 | ≥2.6 |
| Time = 15 min. | ≤0.69 | 20 | ≤1.99 | ≥3.1 |
| Time = 30 min. | ≤0.69 | 20 | ≤1.99 | ≥3.1 |
| Time = 45 min. | ≤0.69 | 20 | ≤1.99 | ≥3.1 |
| Time = 60 min. | ≤1.17 | 20 | ≤2.47 | ≥2.6 |
| Time = 120 min. | ≤0.69 | 20 | ≤1.99 | ≥3.1 |

[a]Titer obtained from $TCID_{50}$ assay.

[b]Dilution factor = 20 (from quenching 1 mL of spiked TA with 19 mL of media).

[c]Titer of sample, adjusted for the dilution factor, obtained by multiplying titer from $TCID_{50}$ assay and the dilution factor from the quench.

$$^{d}RF = \log_{10}\frac{(\text{Input virus titer per mL})\times\text{Input volume}}{(\text{Output virus titer per mL})\times\text{Output volume}}$$

Note:

Input volume = output volume. Final quenched volume of each sample was 20 ml.

[e]Not applicable.

B) Low pH X-MLV Inactivation Experiments

Table 5 shows parameters in low pH virus inactivation studies. Experiments were performed in duplicate.

TABLE 5

Parameters in Low pH Inactivation Studies

| Virology Run No. | Intermediate Process Step | Fcγ-Fcε Concentration (mg/mL) |
|---|---|---|
| 5 | Low pH Inactivation (pH 3.7) | 4.7 |
| 6 | Low pH Inactivation (pH 3.7) | 4.7 |
| 7 | Low pH Inactivation (pH 3.9) | 4.7 |
| 8 | Low pH Inactivation (pH 3.9) | 4.7 |

Figure 3:
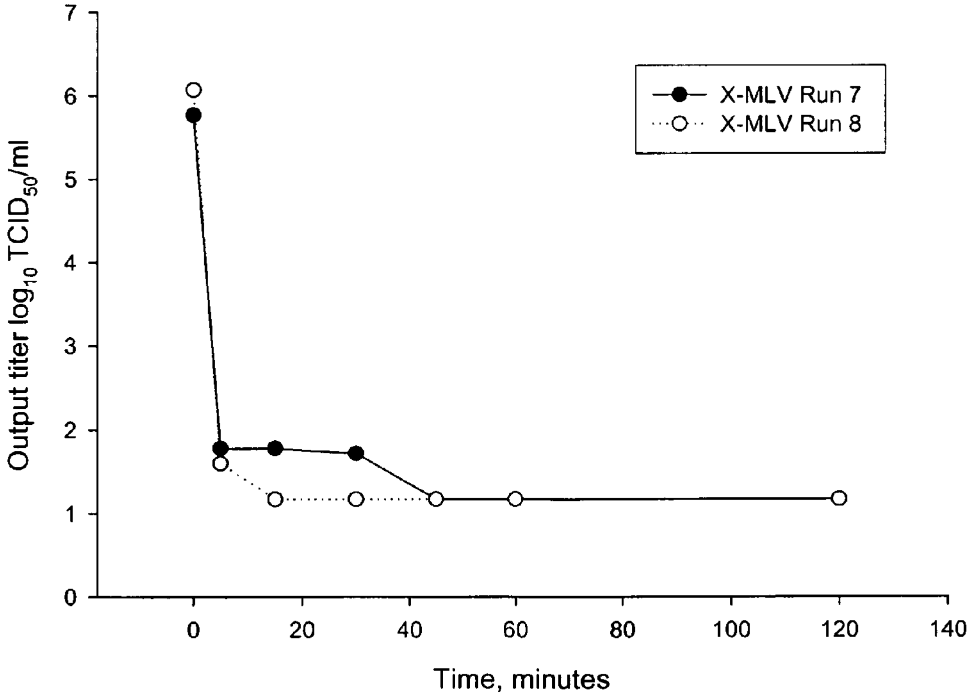
FIG. 3 depicts the kinetics of X-MLV inactivation for Fcγ-Fcϵ (BIIB-016) at pH 3.7. Virus titer at the initial time point (t=0 min) was obtained from the virus control.
Figure 4:
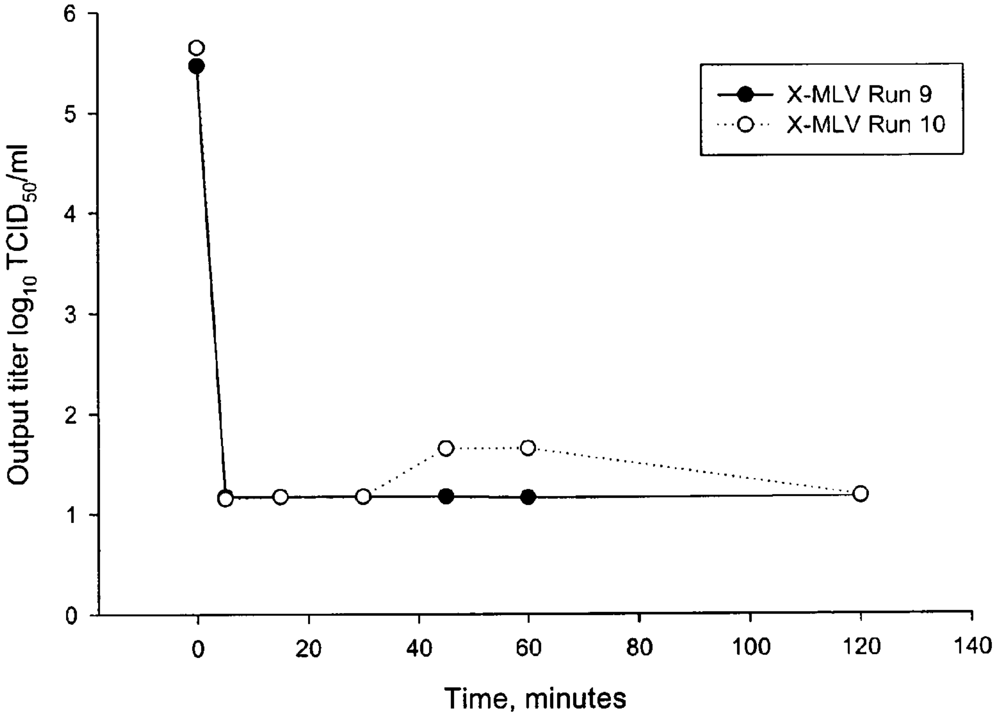
FIG. 4 depicts the kinetics of X-MLV inactivation for Fcγ-Fcϵ (BIIB-016) at pH 3.9. Virus titer at the initial time point (t=0 min) was obtained from the virus control.

For the low pH studies, a summary of the virus inactivation data is shown in Tables 6 and 7. Tables 6 and 7 summarize X-MLV Reduction Factors (RF) at various time points, while Table 13 summarizes RF values following 120 min. of exposure at low pH conditions. FIGS. 3 and 4 show inactivation kinetics of X-MLV for pH 3.7 and 3.9, respectively.

For these low pH inactivation studies, it is important to note that X-MLV in the load and the hold control samples (held at neutral pH) was inactivated. The presence of arginine in the MABSELECT™ eluate may have been responsible for inactivation of the neutral load and hold controls. Therefore, a virus control sample was used to calculate the reduction factors in these studies. The virus control, which was in a neutralized, PG-4 assay medium (without arginine), did not show any significant inactivation during the time course of the study.

At pH 3.7, X-MLV was significantly inactivated following 5 minutes exposure, and below detectable levels following 45 minutes for both of the runs (Table 6, FIG. 3). X-MLV was detectable in one of the runs at pH 3.7 for several time points (Run #5), but within assay variability (<1 $\log_{10}$) of the duplicate run (Run #6), which was below detection for all time points ≥5 minutes.

Similar results were obtained at a higher pH of 3.9, with X-MLV being below detection following 5 minutes exposure for both of the duplicate runs (Table 7 and FIG. 4).

As a result of X-MLV inactivation in the hold and load controls, it was not certain if the low pH conditions were responsible for the observed virus inactivation. The presence of 1M arginine may also have contributed to X-MLV inactivation during the low pH studies.

TABLE 6

X-MLV inactivation data for GE2-Fcγ-Fcϵ samples exposed to pH 3.7

| Sample ID/ Description | Input titer, $Log_{10}$ $TCID_{50}$/mL | Input volume[a], mL | Output titer, $Log_{10}$ $TCID_{50}$/mL | Output volume[b], mL | RF[c] |
|---|---|---|---|---|---|
| Virus Control | 5.77 | N/A[d] | N/A | N/A | N/A |
| Virology Run #5 | | | | | |
| Load Control (T0 min.) | 3.28 | 8 | 3.28 | 8 | 2.5 |
| Hold Control | ≤2.60 | 8 | ≤2.60 | 8 | ≥3.2 |
| Time = 5 min. | | 8 | 1.78 | 8.2 | 4.0 |
| Time = 15 min. | | 8 | 1.78 | 8.2 | 4.0 |
| Time = 30 min. | | 8 | 1.72 | 8.2 | 4.0 |
| Time = 45 min. | | 8 | ≤1.17 | 8.2 | ≥4.6 |
| Time = 60 min. | | 8 | ≤1.17 | 8.2 | ≥4.6 |
| Time = 120 min. | | 8 | ≤1.17 | 8.2 | ≥4.6 |
| Virology Run #6 | | | | | |
| Virus Control | 6.07 | N/A[d] | N/A | N/A | N/A |
| Load Control (Time = 0) | ≤2.60 | 8 | ≤2.60 | 8 | ≥3.5 |
| Hold Control | ≤2.60 | 8 | ≤2.60 | 8 | ≥3.5 |
| Time = 5 min. | | 8 | 1.60 | 8.2 | 4.5 |
| Time = 15 min. | | 8 | ≤1.17 | 8.2 | ≥4.9 |
| Time = 30 min. | | 8 | ≤1.17 | 8.2 | ≥4.9 |
| Time = 45 min. | | 8 | ≤1.17 | 8.2 | ≥4.9 |
| Time = 60 min. | | 8 | ≤1.17 | 8.2 | ≥4.9 |
| Time = 120 min. | | 8 | ≤1.17 | 8.2 | ≥4.9 |

[a]Input volume = volume of collected sample.
[b]Output volume = volume of neutralized sample.
[c]Calculation: $RF = \mathrm{Log}_{10}\frac{(\text{Input virus titer per mL})\times\text{Input volume}}{(\text{Output virus titer per mL})\times\text{Output volume}}$ Note:
Virus Control titers were used for the Input virus titers due to low virus titers in the Load and Hold controls, indicating that the neutralized TA material had a virucidal effect.
[d]Not applicable.

TABLE 7

X-MLV inactivation data for GE2-Fcγ-Fcϵ samples exposed to pH 3.9

| Sample ID/ Description | Input titer, $Log_{10}$ $TCID_{50}$/mL | Input volume[a], mL | Output titer, $Log_{10}$ $TCID_{50}$/mL | Output volume[b], mL | RF[c] |
|---|---|---|---|---|---|
| Virus Control | 5.47 | N/A[d] | N/A | N/A | N/A |
| Virology Run #7 | | | | | |
| Load Control (Time = 0) | ≤2.55 | 8 | ≤2.55 | 8 | ≥2.9 |
| Hold Control | ≤2.60 | 8 | ≤2.60 | 8 | ≥2.9 |
| Time = 5 min. | | 8 | ≤1.17 | 8.2 | ≥4.3 |
| Time = 15 min. | | 8 | ≤1.17 | 8.2 | ≥4.3 |
| Time = 30 min. | | 8 | ≤1.17 | 8.2 | ≥4.3 |

TABLE 7-continued

X-MLV inactivation data for GE2-Fcγ-Fcϵ samples exposed to pH 3.9

| Sample ID/ Description | Input titer, $Log_{10}$ $TCID_{50}$/mL | Input volume[a], mL | Output titer, $Log_{10}$ $TCID_{50}$/mL | Output volume[b], mL | RF[c] |
|---|---|---|---|---|---|
| Time = 45 min. | | 8 | ≤1.17 | 8.2 | ≥4.3 |
| Time = 60 min. | | 8 | ≤1.16 | 8.2 | ≥4.3 |
| Time =120 min. | | 8 | ≤1.17 | 8.2 | ≥4.3 |
| Virology Run #8 | | | | | |
| Virus Control | 5.65 | N/A[d] | N/A | N/A | N/A |
| Load Control (Time = 0) | ≤2.59 | 8 | ≤2.59 | 8 | ≥3.1 |
| Hold Control | ≤2.58 | 8 | ≤2.58 | 8 | ≥3.1 |
| Time = 5 min. | | 8 | ≤1.15 | 8.2 | ≥4.5 |
| Time = 15 min. | | 8 | ≤1.17 | 8.2 | ≥4.5 |
| Time = 30 min. | | 8 | ≤1.17 | 8.2 | ≥4.5 |
| Time = 45 min. | | 8 | ≤1.65 | 8.2 | ≥4.0 |
| Time = 60 min. | | 8 | ≤1.65 | 8.2 | ≥4.0 |
| Time = 120 min. | | 8 | ≤1.18 | 8.2 | ≥4.5 |

[a]Input volume = volume of collected sample.
[b]Output volume = volume of neutralized sample.
[c]Calculation:

$$RF = \mathrm{Log}_{10}\frac{(\text{Input virus titer per mL})\times\text{Input volume}}{(\text{Output virus titer per mL})\times\text{Output volume}}$$

Note:
Virus Control titers were used for the Input virus titers due to low virus titers in the Load and Hold controls, indicating that the neutralized TA material had a virucidal effect.
[d]Not applicable.

C) Arginine X-MLV Inactivation Experiments

Inactivation of X-MLV in the presence of arginine (at neutral pH) was examined both with and without GE2-Fcγ-Fcϵ. Table 8 shows some parameters of arginine inactivation experiments in this Example. Experiments were performed in duplicate. The buffer used for the load and hold control studies did not contain arginine (~5 mM Tris, pH 7.0).

TABLE 8

Parameters in Neutral Arginine Inactivation Studies

| Virology Run No. | Intermediate Process Step | Fcγ-Fcϵ Concentration (mg/mL) |
|---|---|---|
| 9 | Neutralized MABSELECT ™ Eluate Buffer (pH ~7.0) | 0 |
| 10 | Neutralized MABSELECT ™ Eluate Buffer (pH ~7.0) | 0 |
| 11 | Neutralized MABSELECT ™ Eluate Buffer (pH ~7.0) | 3.3 |
| 12 | Neutralized MABSELECT ™ Eluate Buffer (pH ~7.0) | 3.3 |

Figure 5:
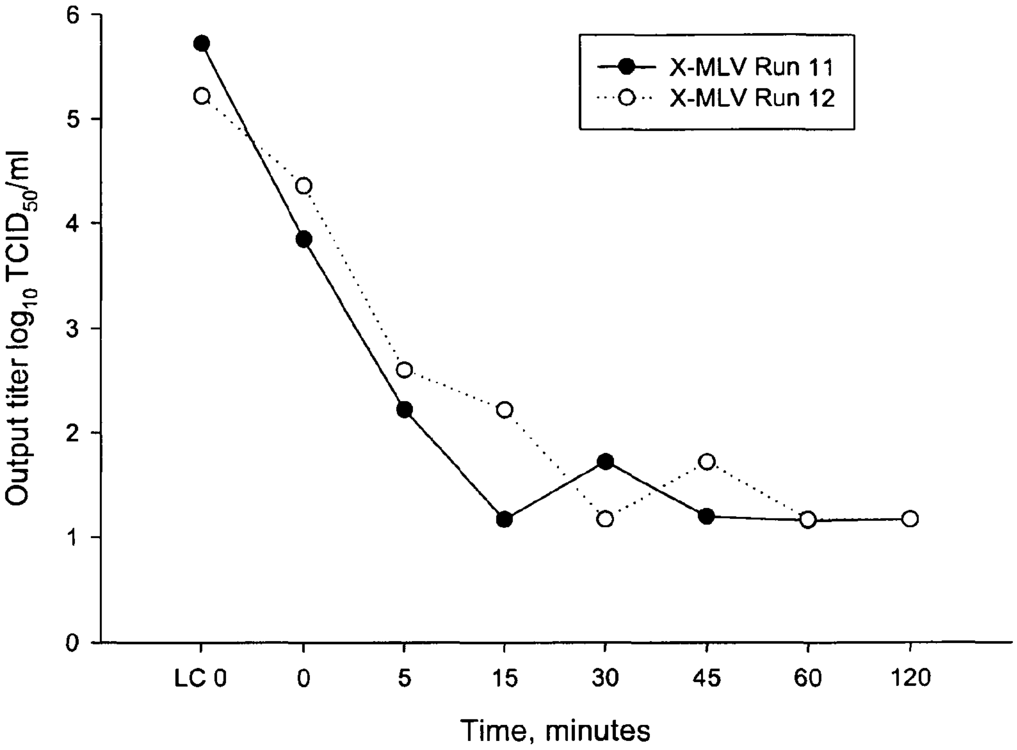
FIG. 5 depicts the kinetics of X-MLV inactivation for Fcγ-Fcϵ (BIIB-016) at neutral pH in 1 M arginine. LC 0=Load Control (Time 0).
Figure 6:
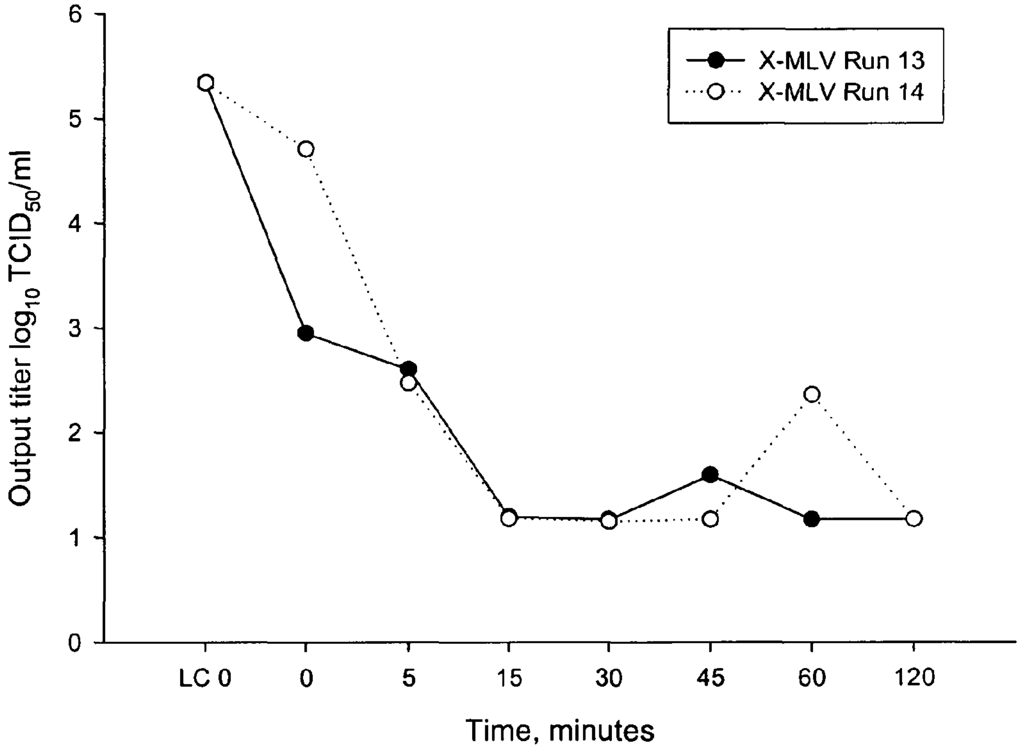
FIG. 6 depicts kinetics of X-MLV inactivation for Fcγ-Fcϵ (BILB-016) at neutral pH in 1 M arginine with Fcγ-Fcϵ. LC 0=Load Control (Time 0).

Tables 11 and 12 summarize X-MLV Reduction Factors (RF) at various time points, while Table 13 summarizes RF values for four runs after 120 min. FIGS. 5 and 6 show the inactivation kinetics of X-MLV in 1 M arginine buffer, in the absence and presence of GE2-Fcγ-Fcϵ, respectively. In this study, X-MLV was at, or below, detectable levels following 15 minutes in neutral solution containing 1 M arginine. However, detectable levels of virus were present after 5 minutes exposure in all of the studies (Runs 9-12). X-MLV inactivation kinetics in the arginine studies were slightly less rapid compared with the inactivation kinetics measured during the low pH studies. However, in both studies, X-MLV levels were at, or below, detection following 30 minutes exposure.

Similar inactivation kinetics were achieved with and without the presence of GE2-Fcγ-Fcϵ (FIGS. 5 and 6) in the arginine buffer. The results indicate that GE2-Fcγ-Fcϵ had no effect on X-MLV inactivation during the studies. It is also important to note the load and hold control samples, which did not contain arginine, did not show any X-MLV inactivation over a 120-minute interval. The apparent inactivation of X-MLV was due to the presence of arginine in the buffer solution. X-MLV Reduction Factors of ≥4.1 were achieved in all of the arginine studies after 120 min of exposure (Table 13).

TABLE 9

X-MLV inactivation data for GE2-Fcγ-Fcϵ neutralized MABSELECT ™ Eluate buffer

| Sample ID/ Description | Input titer, $Log_{10}$ $TCID_{50}$/mL | Input volume[a], mL | Output titer, $Log_{10}$ $TCID_{50}$/mL | Output volume[a], mL | RF[b] |
|---|---|---|---|---|---|
| Virus Control (Time = 0) | 5.98 | N/A[c] | N/A | N/A | N/A |
| Virus Control (Time = 60 min.) | 5.98 | N/A | N/A | N/A | N/A |
| Virus Control (Time = 120 min.) | 5.73 | N/A | N/A | N/A | N/A |
| Virology Run #9 | | | | | |
| Load Control (Time = 0) | 5.72 | N/A | N/A | N/A | N/A |
| Hold Control (Time = 60 min.) | | 8 | 5.22 | 8 | 0.5 |
| Hold Control (Time = 120 min.) | | 8 | 5.61 | 8 | 0.1 |
| Time = 0 min. | | 8 | 3.85 | 8 | 1.9 |
| Time = 5 min. | | 8 | 2.22 | 8 | 3.5 |
| Time = 15 min. | | 8 | ≤1.17 | 8 | ≥4.6 |
| Time = 30 min. | | 8 | 1.72 | 8 | 4.0 |
| Time = 45 min. | | 8 | ≤1.20 | 8 | ≥4.5 |
| Time = 60 min. | | 8 | ≤1.16 | 8 | ≥4.6 |
| Time = 120 min. | | 8 | ≤1.17 | 8 | ≥4.6 |

[a]Input volume = Output volume.

[b]Calculation:

$$RF = \mathrm{Log}_{10}\frac{(\text{Input virus titer per mL}) \times \text{Input volume}}{(\text{Output virus titer per mL}) \times \text{Output volume}}$$

Note:

Load Control (T0) titers were used for the Input virus titers.

[c]Not applicable.

TABLE 10

X-MLV inactivation data for GE2-Fcγ-Fcϵ neutralized MABSELECT ™ Eluate buffer (continued)

| Sample ID/ Description | Input titer, $Log_{10}$ $TCID_{50}$/mL | Input volume[a], mL | Output titer, $Log_{10}$ $TCID_{50}$/mL | Output volume[a], mL | RF[b] |
|---|---|---|---|---|---|
| Virus Control (Time = 0) | 5.48 | N/A[c] | N/A | N/A | N/A |
| Virus Control (Time = 60 min.) | 5.73 | N/A[c] | N/A | N/A | N/A |
| Virus Control (Time = 120 min.) | 5.73 | N/A[c] | N/A | N/A | N/A |
| Virology Run #10 | | | | | |
| Load Control (Time = 0) | 5.22 | N/A | N/A | N/A | N/A |
| Hold Control (Time = 60 min.) | | 8 | 5.49 | 8 | −0.3 |
| Hold Control (Time = 120 min.) | | 8 | 5.22 | 8 | 0.0 |

TABLE 10-continued

X-MLV inactivation data for GE2-Fcγ-Fcϵ neutralized MABSELECT ™ Eluate buffer (continued)

| Sample ID/ Description | Input titer, $Log_{10}$ $TCID_{50}$/mL | Input volume[a], mL | Output titer, $Log_{10}$ $TCID_{50}$/mL | Output volume[a], mL | RF[b] |
|---|---|---|---|---|---|
| Time = 0 | | 8 | 4.36 | 8 | 0.9 |
| Time = 5 min. | | 8 | 2.60 | 8 | 2.6 |
| Time = 15 min. | | 8 | 2.22 | 8 | 3.0 |
| Time = 30 min. | | 8 | ≤1.17 | 8 | ≥4.1 |
| Time = 45 min. | | 8 | 1.72 | 8 | 3.5 |
| Time = 60 min. | | 8 | ≤1.17 | 8 | ≥4.1 |
| Time = 120 min. | | 8 | ≤1.17 | 8 | ≥4.1 |

[a]Input volume = Output volume.

[b]Calculation:

$$RF = \mathrm{Log}_{10}\frac{(\text{Input virus titer per mL}) \times \text{Input volume}}{(\text{Output virus titer per mL}) \times \text{Output volume}}$$

Note:

Load Control (T0) titers were used for the Input virus titers.

[c]Not applicable.

TABLE 11

X-MLV inactivation data for neutralized MABSELECT ™ buffer with GE2-Fcγ-Fcϵ

| Sample ID/ Description | Input titer, $Log_{10}$ $TCID_{50}$/mL | Input volume[a], mL | Output titer, $Log_{10}$ $TCID_{50}$/mL | Output volume[a], mL | RF[b] |
|---|---|---|---|---|---|
| Virus Control (Time = 0) | 5.60 | N/A[c] | N/A | N/A | N/A |
| Virus Control (Time = 60) | 5.35 | N/A[c] | N/A | N/A | N/A |
| Virus Control (Time = 120) | 5.98 | N/A[c] | N/A | N/A | N/A |
| Virology Run #11 | | | | | |
| Load Control (Time = 0) | 5.35 | N/A | N/A | N/A | N/A |
| Hold Control (Time = 60) | | 8 | 5.21 | 8 | 0.1 |
| Hold Control (Time = 120) | | 8 | 5.22 | 8 | 0.1 |
| Time = 0 | | 8 | 2.95 | 8 | 2.4 |
| Time = 5 | | 8 | 2.60 | 8 | 2.8 |
| Time = 15 | | 8 | ≤1.20 | 8 | ≥4.2 |
| Time = 30 | | 8 | ≤1.17 | 8 | ≥4.2 |
| Time = 45 | | 8 | 1.59 | 8 | 3.8 |
| Time = 60 | | 8 | ≤1.17 | 8 | ≥4.2 |
| Time = 120 | | 8 | ≤1.17 | 8 | ≥4.2 |

[a]Input volume = Output volume.

[b]Calculation:

$$RF = \mathrm{Log}_{10}\frac{(\text{Input virus titer per mL}) \times \text{Input volume}}{(\text{Output virus titer per mL}) \times \text{Output volume}}$$

Note:

Load Control (T0) titers were used for the Input virus titers.

[c]Not applicable.

TABLE 12

X-MLV inactivation data for neutralized MABSELECT ™ buffer with GE2-Fcγ-Fcϵ (continued)

| Sample ID/ Description | Input titer, $Log_{10}$ $TCID_{50}$/mL | Input volume[a], mL | Output titer, $Log_{10}$ $TCID_{50}$/mL | Output volume[a], mL | RF[b] |
|---|---|---|---|---|---|
| Virus Control (Time = 0) | 5.85 | N/A[c] | N/A | N/A | N/A |
| Virus Control (Time = 60 min.) | 5.60 | N/A | N/A | N/A | N/A |
| Virus Control (Time = 120 min.) | 5.23 | N/A | N/A | N/A | N/A |
| Virology Run 12 | | | | | |
| Load Control (Time = 0) | 5.34 | N/A | N/A | N/A | N/A |
| Hold Control (Time = 60 min.) | | 8 | 5.48 | 8 | −0.1 |
| Hold Control (Time = 120 min.) | | 8 | 5.60 | 8 | −0.3 |
| Time = 0 | | 8 | 4.71 | 8 | 0.6 |
| Time = 5 min. | | 8 | 2.47 | 8 | 2.9 |
| Time = 15 min. | | 8 | ≤1.18 | 8 | ≥4.2 |
| Time = 30 min. | | 8 | ≤1.15 | 8 | ≥4.2 |
| Time = 45 min. | | 8 | ≤1.17 | 8 | ≥4.2 |
| Time = 60 min. | | 8 | 2.36 | 8 | 3.0 |
| Time = 120 min. | | 8 | ≤1.17 | 8 | ≥4.2 |

[a]Input volume = Output volume.

[b]Calculation:

$$RF = Log_{10}\frac{(\text{Input virus titer per mL}) \times \text{Input volume}}{(\text{Output virus titer per mL}) \times \text{Output volume}}$$

Note:

Load Control (T0) titers were used for the Input virus titers.

[c]Not applicable.

TABLE 13

Summary of X-MLV inactivation studies

| Run number | Study Description | Fcγ-Fcϵ Concentration (mg/mL) | pH | Input virus titer, $log_{10}$ $TCID_{50}$/mL | Output virus titer, $log_{10}$ $TCID_{50}$/mL[a] | Virus inactivation, RF[b] |
|---|---|---|---|---|---|---|
| 1 | TRITON ® (0.10%) | 1.13 | ~7 | 5.35 | ≤1.99 | ≥3.4 |
| 2 | TRITON ® (0.10%) | 1.13 | ~7 | 5.06 | ≤1.99 | ≥3.1 |
| 3 | TRITON ® (0.20%) | 1.12 | ~7 | 5.06 | ≤2.47 | ≥2.6 |
| 4 | TRITON ® (0.20%) | 1.12 | ~7 | 5.06 | ≤1.99 | ≥3.1 |
| 5 | Low pH | 4.7 | 3.7 | 5.77[c] | ≤1.17 | ≥4.6 |
| 6 | Low pH | 4.7 | 3.7 | 6.07[c] | ≤1.17 | ≥4.9 |
| 7 | Low pH | 4.7 | 3.9 | 5.47[c] | ≤1.17 | ≥4.3 |
| 8 | Low pH | 4.7 | 3.9 | 5.65[c] | ≤1.18 | ≥4.5 |
| 9 | Arginine (1M) | 0 | ~7 | 5.72 | ≤1.17 | ≥4.6 |
| 10 | Arginine (1M) | 0 | ~7 | 5.22 | ≤1.17 | ≥4.1 |
| 11 | Arginine (1M) | 3.3 | ~7 | 5.35 | ≤1.17 | ≥4.2 |

TABLE 13-continued

Summary of X-MLV inactivation studies

| Run number | Study Description | Fcγ-Fcϵ Concentration (mg/mL) | pH | Input virus titer, $log_{10}$ $TCID_{50}$/mL | Output virus titer, $log_{10}$ $TCID_{50}$/mL[a] | Virus inactivation, RF[b] |
|---|---|---|---|---|---|---|
| 12 | Arginine (1M) | 3.3 | ~7 | 5.34 | ≤1.17 | ≥4.2 |

[a]Output Virus titer represents the last time point (120 minutes) for each study

[b]Calculation:

$$RF = Log_{10}\frac{(\text{Input virus titer per mL}) \times \text{Input volume}}{(\text{Output virus titer per mL}) \times \text{Output volume}}$$

[c]Virus Control titers were used for the Input virus titers due to low virus titers in the Load and Hold controls, indicating that the neutralized TA material had a virucidal effect.

Example 2

Arginine and Glycine Virus Inactivation Studies with X-MLV, SuHV-1 and MMV

To further characterize the virus inactivation kinetics of arginine, and identify viruses inactivated by arginine, three viruses were tested (X-MLV, SuHV-1 and MMV) in the presence of high concentrations of two amino acids (arginine and glycine) at neutral pH. All studies were performed at 2-8° C. Experimental parameters of these studies are shown in Table 14. Each experiment was performed in duplicate.

TABLE 14

Buffers and Viruses Evaluated in the Virus Inactivation Studies

| Study # | Run # | Study # | Buffer Composition | Virus |
|---|---|---|---|---|
| 1 | 1, 2 | 1 | 5 mM Tris + 0.10M Arginine-HCl (pH 7.0) | X-MLV |
| 2 | 3, 4 | 2 | 5 mM Tris + 0.50M Arginine-HCl (pH 7.0) | X-MLV |
| 3 | 5, 6 | 3 | 5 mM Tris + 1.0M Arginine-HCl (pH 7.0) | SuHV-1 |
| 4 | 7, 8 | 4 | 5 mM Tris + 1.0M Arginine-HCl (pH 7.0) | MMV |
| 5 | 9, 10 | 5 | 50 mM Histidine + 50 mM CaCl2 + 1.0M Arginine + 0.04% Tween-80 + 50% Propylene Glycol (pH 7.0) | X-MLV |
| 6 | 11, 12 | 6 | 50 mM Histidine + 50 mM CaCl2 + 1.0M Arginine + 0.04% Tween-80 + 50% Propylene Glycol (pH 7.0) | SuHV-1 |
| 7 | 13, 14 | 7 | 5 mM Tris + 1.0M Glycine (pH 7.0) | X-MLV |

X-MLV was chosen as a model retrovirus for this study as representative of endogenous retroviruses commonly found in mammalian cell culture. The additional model viruses selected for the study comprise a wide range of virus characteristics. The viruses evaluated were xenotropic Murine leukemia virus (X-MLV), Murine minute virus (MMV), and Suid herpesvirus 1 (SuHV-1) (Table 15).

TABLE 15

| Characteristics of model viruses | | | | | | |
|---|---|---|---|---|---|---|
| Virus | Genome | Envelope | Family Genus | Size (nm) | Shape | Resistance to Physico-chemical Treatment |
| X-MLV | RNA | Yes | Retroviridae Gammaretrovirus | 80-110 | Spherical | Low |
| MMV | DNA | No | Parvoviridae Parvovirus | 18-24 | Icosahedral | Very High |
| SuHV-1 | DNA | Yes | Herpesviridae Varicellovirus | 120-200 | Spherical | Medium |

A) X-MLV in the Presence of 0.1 M Arginine

Figure 7:
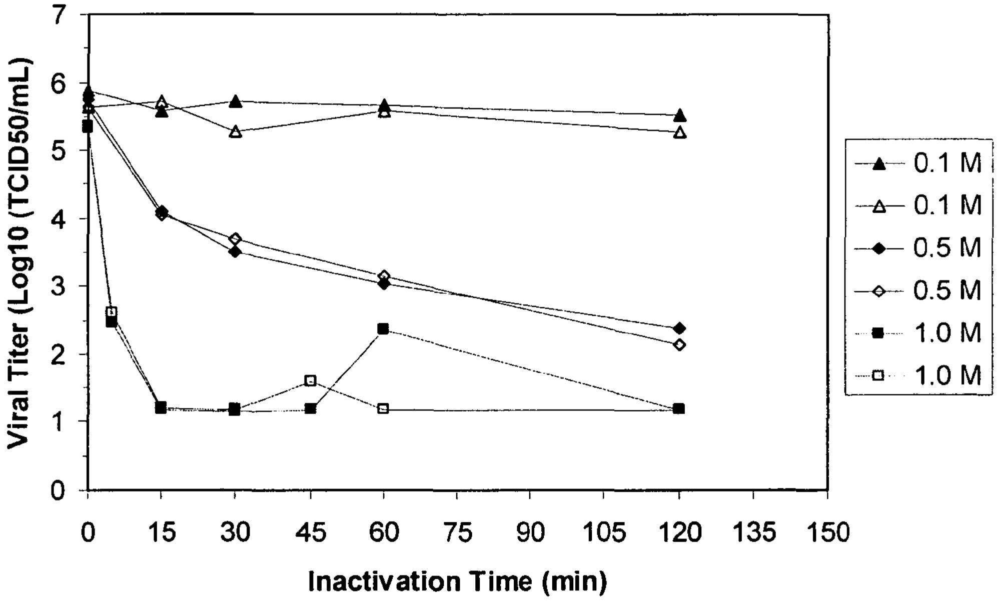
FIG. 7 depicts kinetics of X-MLV inactivation using: (a). 0.1 M arginine, (b). 0.5 M arginine and (c). 1.0 M arginine in a 5 mM Tris (pH 7.0) buffer.

In the presence of 0.1 M arginine (at pH 7.0) (Table 14), X-MLV inactivation did not occur after 120 minutes of exposure in duplicate runs (Table 16, FIG. 7), as virus titer levels did not significantly change over the evaluated time. A plot of the X-MLV inactivation kinetics is shown in FIG. 7. Results of the study showed the presence 0.1 M arginine at neutral pH (7.0) was not a concentration sufficient to effectively inactivate X-MLV over a 120 min hold.

TABLE 16

| Kinetics of X-MLV inactivation Using 0.1M Arginine Buffer | | |
|---|---|---|
| Sample ID/ Description | Sample Titer, $Log_{10}$ $TCID_{50}$/mL | RF[b] |
| Run 1 | | |
| Virus Control | 6.25 | N/A |
| Load Control | 5.88 | N/A |
| Hold Control | ND[a] | N/A |
| Time = 15 min. | 5.59 | 0.3 |
| Time = 30 min. | 5.71 | 0.2 |
| Time = 60 min. | 5.65 | 0.2 |
| Time = 120 min. | 5.53 | 0.3 |
| Run 2 | | |
| Load Control | 5.63 | N/A |
| Hold Control | ND[a] | N/A |
| Time = 15 min. | 5.71 | −0.1 |
| Time = 30 min. | 5.29 | 0.3 |
| Time = 60 min. | 5.29 | 0.0 |
| Time = 120 min. | 5.29 | 0.3 |

[a]Not Determined $$^{b}RF = \log_{10}\frac{(\text{Input virus titer per mL})}{(\text{Ouput virus titer per mL})}$$

Note:
Input volume = output volume.

B) X-MLV in the Presence of 0.5 M Arginine

In the presence of 0.5 M arginine (at pH 7.0) (Table 14), X-MLV virus titer decreased over the 120 minutes of exposure time (Table 17). A plot of the X-MLV inactivation kinetics is shown in FIG. 7. Reduction factors of 3.4 and 3.5 for X-MLV were achieved in the two runs after 120 minutes of exposure. Although virus titers were decreased, detectable levels were present after 120 minutes of exposure, which indicated some inactivation did occur in the presence of 0.5 M arginine.

TABLE 17

| Kinetics of X-MLV inactivation Using 0.5M Arginine Buffer | | |
|---|---|---|
| Sample ID/ Description | Sample Titer, $Log_{10}$, $TCID_{50}$/mL | RF[b] |
| Run 1 | | |
| Virus Control | 6.00 | N/A |
| Load Control | 5.75 | N/A |
| Hold Control | ND[a] | N/A |
| Time = 15 min. | 4.10 | 1.7 |
| Time = 30 min. | 3.50 | 2.3 |
| Time = 60 min. | 3.03 | 2.7 |
| Time = 120 min. | 2.37 | 3.4 |
| Run 2 | | |
| Load Control | 5.63 | N/A |
| Hold Control | ND[a] | N/A |
| Time = 15 min. | 4.04 | 1.6 |
| Time = 30 min. | 3.68 | 2.0 |
| Time = 60 min. | 3.15 | 2.5 |
| Time = 120 min. | 2.13 | 3.5 |

[a]Not Determined $$^{b}RF = \log_{10}\frac{(\text{Input virus titer per mL})}{(\text{Ouput virus titer per mL})}$$

Note:
Input volume = output volume.

C) SuHV-1 in the Presence of 1.0 M Arginine

Figure 8:
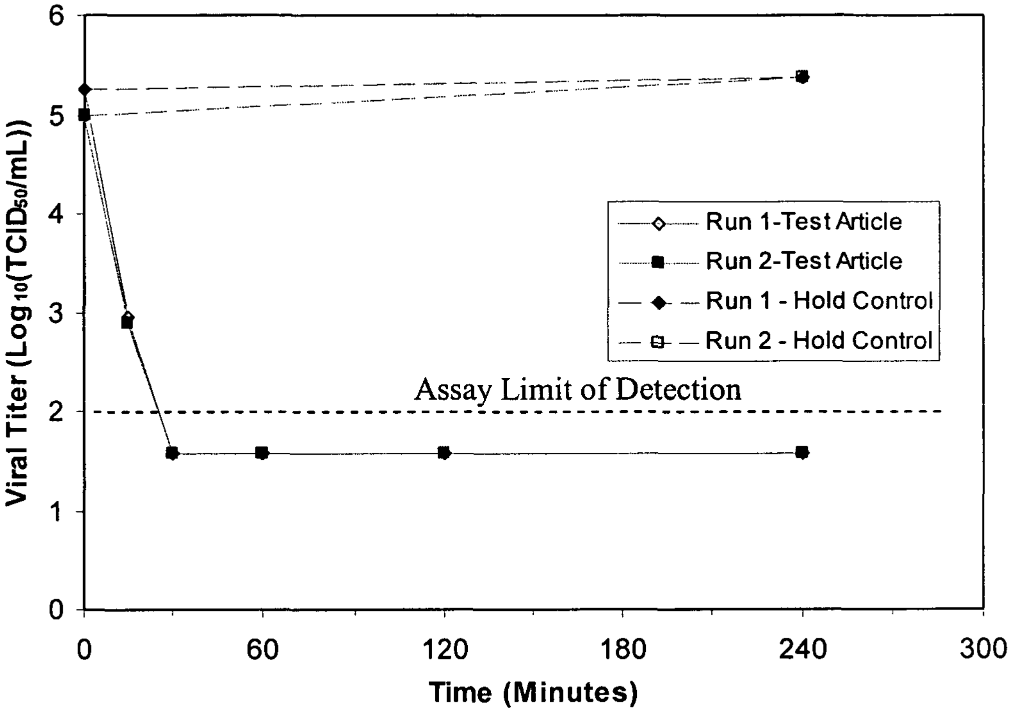
FIG. 8 depicts the kinetics of SuHV-1 inactivation using 1.0 M arginine buffer.

In the presence of 1.0 M arginine (at pH 7.0) (Table 14), SuHV-1 virus titer was below the assay limit of detection following 30 minutes of exposure in duplicate runs (Table 18). A plot of the SuHV-1 inactivation kinetics is shown in FIG. 8. Reduction Factors of ≥3.68 and ≥3.43 for SuHV-1 were achieved in the two runs after 240 minutes of exposure. Results of the study showed the presence of high concentrations of arginine (1.0 M) at neutral pH (7.0) were sufficient to effectively inactivate the SuHV-1 virus with relatively rapid kinetics.

TABLE 18

| Inactivation of SuHV-1 in the presence of arginine | | | | |
|---|---|---|---|---|
| Sample ID/ Description | Titer of quenched sample, $Log_{10}$ $TCID_{50}$/mL[a] | Dilution factor from quench[b] | Adjusted titer of sample, $Log_{10}$ $TCID_{50}$/mL[c] | RF[d] |
| Run 1 | | | | |
| Virus Control | 5.25 | N/A[e] | 5.25 | N/A |
| Load Control | 4.25 | 10 | 5.25 | N/A |
| Hold Control | 4.38 | 10 | 5.38 | −0.13 |
| Time = 15 min. | 1.95 | 10 | 2.95 | 2.30 |
| Time = 30 min. | ≤0.57 | 10 | ≤1.57 | ≥3.68 |
| Time = 60 min. | ≤0.57 | 10 | ≤1.57 | ≥3.68 |

TABLE 18-continued

| Inactivation of SuHV-1 in the presence of arginine | | | | |
|---|---|---|---|---|
| Sample ID/ Description | Titer of quenched sample, $Log_{10}$ $TCID_{50}/mL^a$ | Dilution factor from quench$^b$ | Adjusted titer of sample, $Log_{10}$ $TCID_{50}/mL^c$ | $RF^d$ |
| Time = 120 min. | ≤0.57 | 10 | ≤1.57 | ≥3.68 |
| Time = 240 min. (quenched) | ≤0.57 | 10 | ≤1.57 | ≥3.68 |
| Time = 240 min. (non-quenched)* | ≤1.53 | N/A$^e$ | ≤1.53 | ≥3.72 |
| Run 2 | | | | |
| Load Control | 4.00 | 10 | 5.00 | N/A |
| Hold Control | 4.38 | 10 | 5.38 | −0.38 |
| Time = 15 min. | 1.89 | 10 | 2.89 | 2.11 |
| Time = 30 min. | ≤0.57 | 10 | ≤1.57 | ≥3.43 |
| Time = 60 min. | ≤0.57 | 10 | ≤1.57 | ≥3.43 |
| Time = 120 min. | ≤0.57 | 10 | ≤1.57 | ≥3.43 |
| Time = 240 min. (quenched) | ≤0.57 | 10 | ≤1.57 | ≥3.43 |
| Time = 240 min. (non-quenched)* | ≤1.53 | N/A$^e$ | ≤1.53 | ≥3.47 |

$^a$Titer obtained from $TCID_{50}$ assay.

$^b$Dilution factor = 10 (from quenching 1 mL of spiked TA with 9 mL of media).

$^c$Titer of sample, adjusted for the dilution factor, obtained by multiplying titer from $TCID_{50}$ assay and the dilution factor from the quench, if appropriate.

$${}^dRF = \log_{10}\frac{(\text{Input virus titer per mL})}{(\text{Ouput virus titer per mL})}$$

Note:

Input volume = output volume.

$^e$Not applicable; there is no quench for this sample so dilution factor is 1.

D) MMV in the Presence of 1.0 M Arginine

Figure 9:
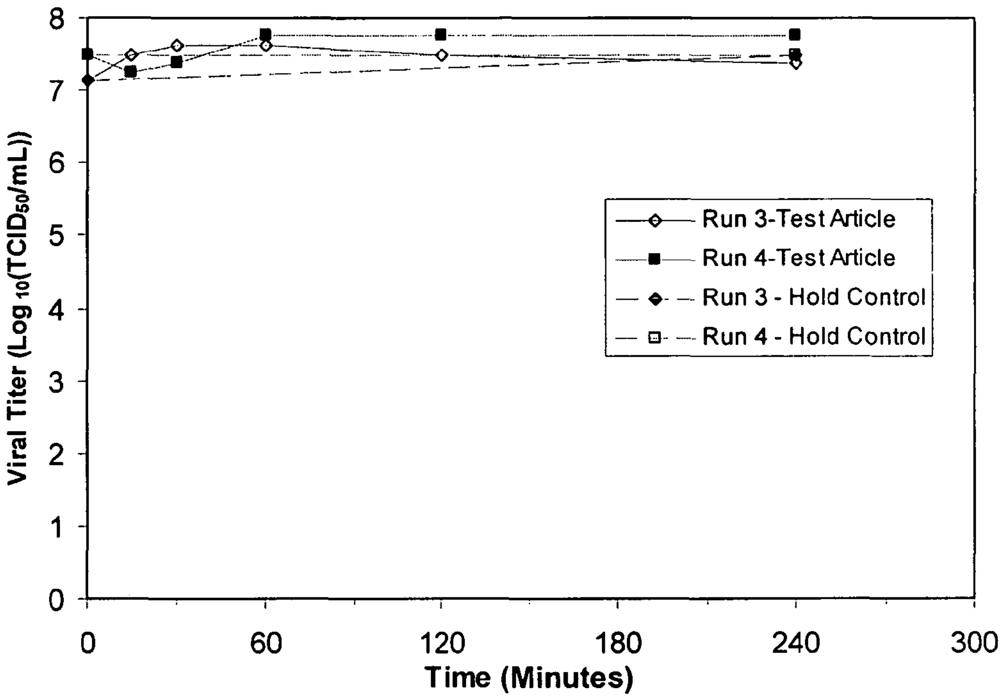
FIG. 9 depicts the kinetics of MMV inactivation using 1.0 M arginine buffer.

MMV was not inactivated in the presence of 1.0 M arginine (Table 14) over a 4 hour period (Table 19). MMV titers measured at various time points over the course of the process had similar levels as the load and hold controls (FIG. 9). The results show that MMV, a non-enveloped virus, was not inactivated in the presence of 1.0 M arginine at pH 7.0.

TABLE 19

| MMV Inactivation in the presence of arginine | | | | |
|---|---|---|---|---|
| Sample ID/ Description | Titer of quenched sample, $Log_{10}$ $TCID_{50}/mL^a$ | Dilution factor from quench$^b$ | Adjusted titer of sample, $Log_{10}$ $TCID_{50}/mL^c$ | $RF^d$ |
| Sample ID: V0800001370-XX | | | | |
| Run 3 | | | | |
| Virus Control | 7.13 | N/A$^e$ | 7.13 | N/A |
| Load Control | 6.13 | 10 | 7.13 | N/A |
| Hold Control | 6.50 | 10 | 7.50 | −0.37 |
| Time = 15 min. | 6.50 | 10 | 7.50 | −0.37 |
| Time = 30 min. | 6.63 | 10 | 7.63 | −0.50 |
| Time = 60 min. | 6.63 | 10 | 7.63 | −0.50 |
| Time = 120 min. | 6.50 | 10 | 7.50 | −0.37 |
| Time = 240 min. (quenched) | 6.38 | 10 | 7.38 | −0.25 |
| Time = 240 min. (non-quenched)* | 6.83 | N/A$^e$ | 6.83 | 0.30 |
| Run 4 | | | | |
| Load Control | 6.50 | 10 | 7.50 | N/A |
| Hold Control | 6.50 | 10 | 7.50 | 0.0 |
| Time = 15 min. | 6.25 | 10 | 7.25 | 0.25 |
| Time = 30 min. | 6.38 | 10 | 7.38 | 0.12 |
| Time = 60 min. | 6.75 | 10 | 7.75 | −0.25 |
| Time = 120 min. | 6.75 | 10 | 7.75 | −0.25 |
| Time = 240 min. (quenched) | 6.75 | 10 | 7.75 | −0.25 |

TABLE 19-continued

| MMV Inactivation in the presence of arginine | | | | |
|---|---|---|---|---|
| Sample ID/ Description | Titer of quenched sample, $Log_{10}$ $TCID_{50}/mL^a$ | Dilution factor from quench$^b$ | Adjusted titer of sample, $Log_{10}$ $TCID_{50}/mL^c$ | $RF^d$ |
| Time = 240 min. (non-quenched)* | 7.33 | N/A$^e$ | 7.33 | 0.17 |

$^a$Titer obtained from $TCID_{50}$ assay.

$^b$Dilution factor = 10 (from quenching 1 mL of spiked TA with 9 mL of media).

$^c$Titer of sample, adjusted for the dilution factor. Obtained by multiplying titer from $TCID_{50}$ assay and the dilution factor from the quench, if appropriate.

$${}^dRF = \log_{10}\frac{(\text{Input virus titer per mL})}{(\text{Ouput virus titer per mL})}$$

Note:

Input volume = output volume.

$^e$Not applicable; there is no quench for this sample so dilution factor is 1.

E) X-MLV in the Presence of 1.0 M Arginine and 50% Propylene Glycol

Figure 10:
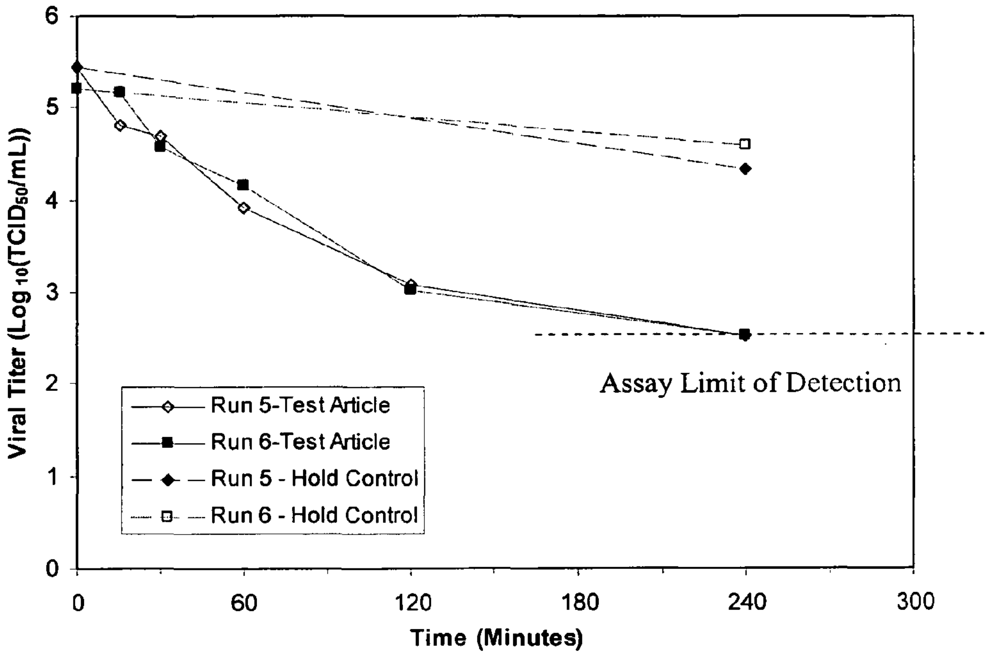
FIG. 10 depicts kinetics of X-MLV inactivation using 1.0 M arginine buffer and 50% propylene glycol.

In the presence of 1.0 M arginine (at pH 7.0) and 50% propylene glycol (Table 14), the X-MLV titer was below the assay limit of detection following 240 minutes of exposure in duplicate runs (Table 20). A relatively slow but steady inactivation occurred during the process (FIG. 10). Reduction factors (RF) of ≥1.80 and ≥2.05 for X-MLV were achieved in the two runs after 240 minutes of exposure. It is noted the RF values were calculated using input virus titers from the Hold Control sample, since the difference in virus titer was >1.0 $log_{10}$ between the Load and the Hold control. The presence of 50% propylene glycol may have slowed the virus inactivation rate, compared with a buffer containing only 1.0 M arginine.

TABLE 20

| Inactivation of X-MLV in Factor VIII Affinity Resin Eluate Buffer | | | | |
|---|---|---|---|---|
| Sample ID/ Description | Titer of quenched sample, $Log_{10}$ $TCID_{50}/mL^a$ | Dilution factor from quench$^b$ | Adjusted titer of sample, $Log_{10}$ $TCID_{50}/mL^c$ | $RF^d$ |
| Run 5 | | | | |
| Virus Control | 5.60 | N/A$^e$ | 5.60 | N/A |
| Load Control | 4.45 | 10 | 5.45 | N/A |
| Hold Control | 3.33 | 10 | 4.33 | N/A |
| Time = 15 | 3.80 | 10 | 4.80 | −0.47 |
| Time = 30 | 3.68 | 10 | 4.68 | −0.35 |
| Time = 60 | 2.91 | 10 | 3.91 | 0.42 |
| Time = 120 | 2.07 | 10 | 3.07 | 1.26 |
| Time = 240 (quenched) | ≤1.53 | 10 | ≤2.53 | ≥1.80 |
| Time = 240 (non-quenched)* | N/D | N/D | N/D | N/D |
| Run 6 | | | | |
| Load Control | 4.20 | 10 | 5.20 | N/A |
| Hold Control | 3.58 | 10 | 4.58 | N/A |
| Time = 15 | 4.16 | 10 | 5.16 | −0.58 |
| Time = 30 | 3.56 | 10 | 4.56 | 0.02 |
| Time = 60 | 3.15 | 10 | 4.15 | 0.43 |
| Time = 120 | 2.01 | 10 | 3.01 | 1.57 |
| Time = 240 (quenched) | ≤1.53 | 10 | ≤2.53 | ≥2.05 |

TABLE 20-continued

| Inactivation of X-MLV in Factor VIII Affinity Resin Eluate Buffer | | | | |
|---|---|---|---|---|
| Sample ID/ Description | Titer of quenched sample, $Log_{10}$ $TCID_{50}/mL^a$ | Dilution factor from quench[b] | Adjusted titer of sample, $Log_{10}$ $TCID_{50}/mL^c$ | RF[d] |
| Time = 240 (non-quenched)* | N/D | N/D | N/D | N/D |

[a]Titer obtained from $TCID_{50}$ assay.

[b]Dilution factor = 10 (from quenching 1 mL of spiked TA with 9 mL of media).

[c]Titer of sample, adjusted for the dilution factor, obtained by multiplying titer from $TCID_{50}$ assay and the dilution factor from the quench, if appropriate.

$$^dRF = \log_{10}\frac{(\text{Input virus titer per mL})}{(\text{Ouput virus titer per mL})}$$

Note:

Input volume = output volume. Hold control titer was used as input, since the Hold control titer was lower than the Load control titer by >0.5 $\log_{10}$.

[e]Not applicable.

"N/D" = Not determined; no sample was collected.

F) SuHV-1 in the Presence of 1.0 M Arginine and 50% Propylene Glycol

Figure 11:
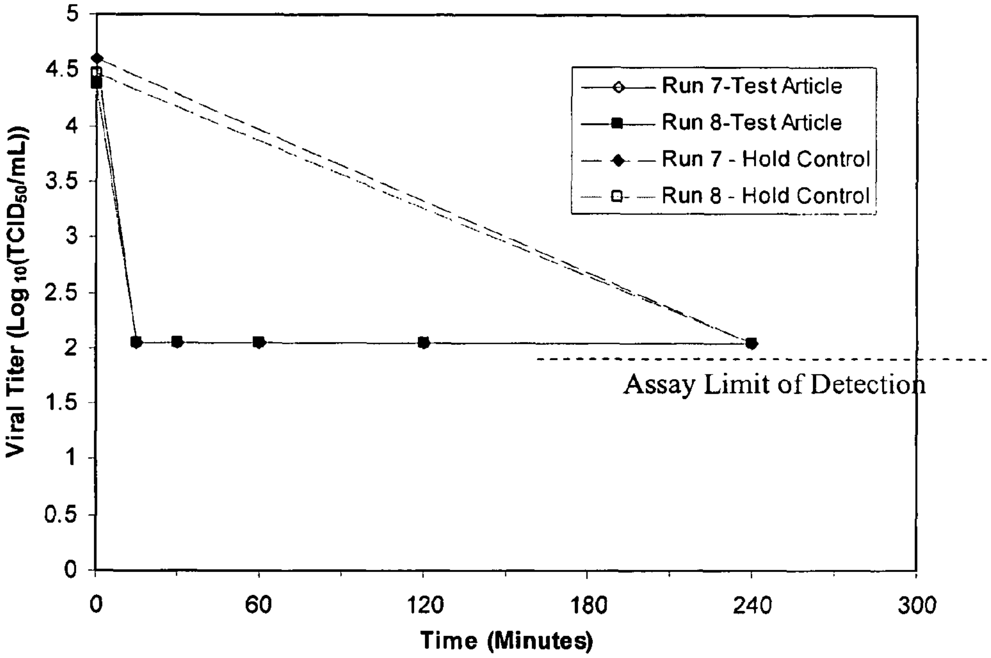
FIG. 11 depicts kinetics of SuHV1 inactivation using 1.0 M arginine buffer and 50% propylene glycol.

In the presence of 1.0 M arginine (at pH 7.0) and 50% propylene glycol (Table 14), SuHV-1 deactivated rapidly, as virus levels were below detection following 15 min of exposure. It is important to note that virus titers in the hold control were also below detection, so the presence of propylene glycol may have contributed to the inactivation process. Reduction factors (RF) of ≥2.55 for SuHV-1 were achieved in the two runs, using the Load control in the RF calculation. The Load control was used to calculate RF since virus titers in the Hold control were below detection. A plot of the inactivation kinetics is shown in FIG. 11.

TABLE 21

| Inactivation of SuHV-1 in Factor VIII Affinity Resin Eluate Buffer | | | | |
|---|---|---|---|---|
| Sample ID/ Description | Titer of quenched sample, $Log_{10}$ $TCID_{50}/mL^a$ | Dilution factor from quench[b] | Adjusted titer of sample, $Log_{10}$ $TCID_{50}/mL^e$ | RF[d] |
| Run 7 | | | | |
| Virus Control | 5.35 | N/A[e] | 5.35 | N/A |
| Load Control | 3.60 | 10 | 4.60 | N/A |
| Hold Control | ≤1.05 | 10 | ≤2.05 | ≥2.55 |
| Time = 15 | ≤1.05 | 10 | ≤2.05 | ≥2.55 |
| Time = 30 | ≤1.05 | 10 | ≤2.05 | ≥2.55 |
| Time = 60 | ≤1.05 | 10 | ≤2.05 | ≥2.55 |
| Time = 120 | ≤1.05 | 10 | ≤2.05 | ≥2.55 |
| Time = 240 (quenched) | ≤1.05 | 10 | ≤2.05 | ≥2.55 |
| Time = 240 (non-quenched)* | N/D | N/D | N/D | N/D |
| Run 8 | | | | |
| Load Control | 3.48 | 10 | 4.48 | N/A |
| Hold Control | ≤1.05 | 10 | ≤2.05 | ≥2.43 |
| Time = 15 | ≤1.05 | 10 | ≤2.05 | ≥2.43 |
| Time = 30 | ≤1.05 | 10 | ≤2.05 | ≥2.43 |
| Time = 60 | ≤1.05 | 10 | ≤2.05 | ≥2.43 |
| Time = 120 | ≤1.05 | 10 | ≤2.05 | ≥2.43 |
| Time = 240 (quenched) | ≤1.05 | 10 | ≤2.05 | ≥2.43 |

TABLE 21-continued

| Inactivation of SuHV-1 in Factor VIII Affinity Resin Eluate Buffer | | | | |
|---|---|---|---|---|
| Sample ID/ Description | Titer of quenched sample, $Log_{10}$ $TCID_{50}/mL^a$ | Dilution factor from quench[b] | Adjusted titer of sample, $Log_{10}$ $TCID_{50}/mL^e$ | RF[d] |
| Time = 240 (non-quenched)* | N/D | N/D | N/D | N/D |

[a]Titer obtained from $TCID_{50}$ assay.

[b]Dilution factor = 10 (from quenching 1 mL of spiked TA with 9 mL of media).

[c]Titer of sample, adjusted for the dilution factor, obtained by multiplying titer from $TCID_{50}$ assay and the dilution factor from the quench, if appropriate.

$$^dRF = \log_{10}\frac{(\text{Input virus titer per mL})}{(\text{Ouput virus titer per mL})}$$

Note:

Input volume = output volume. The Load control was used as the input for these runs, since the Hold control was completely inactivated. This indicates that the Factor VIII Affinity Resin Eluate Buffer, with or without arginine, inactivates SuHV-1.

[e]Not applicable.

"N/D" = Not determined; no sample was collected.

G) XMLV in the Presence of 1.0 M Glycine

Figure 12:
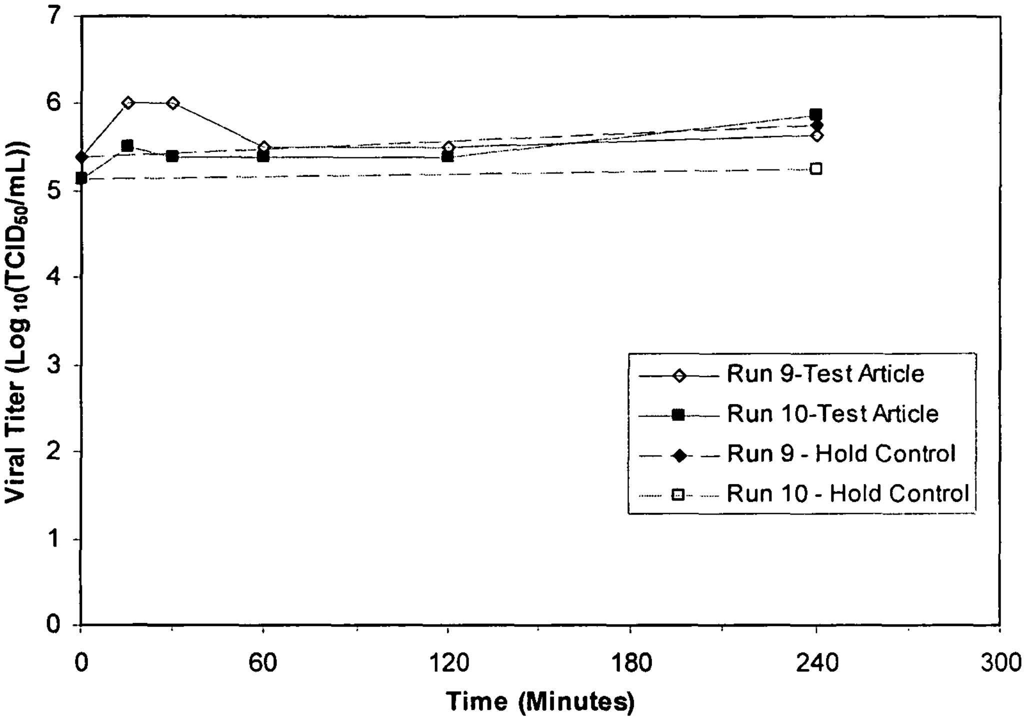
FIG. 12 depicts kinetics of X-MLV inactivation using 1.0 M glycine buffer.
Figure 13:
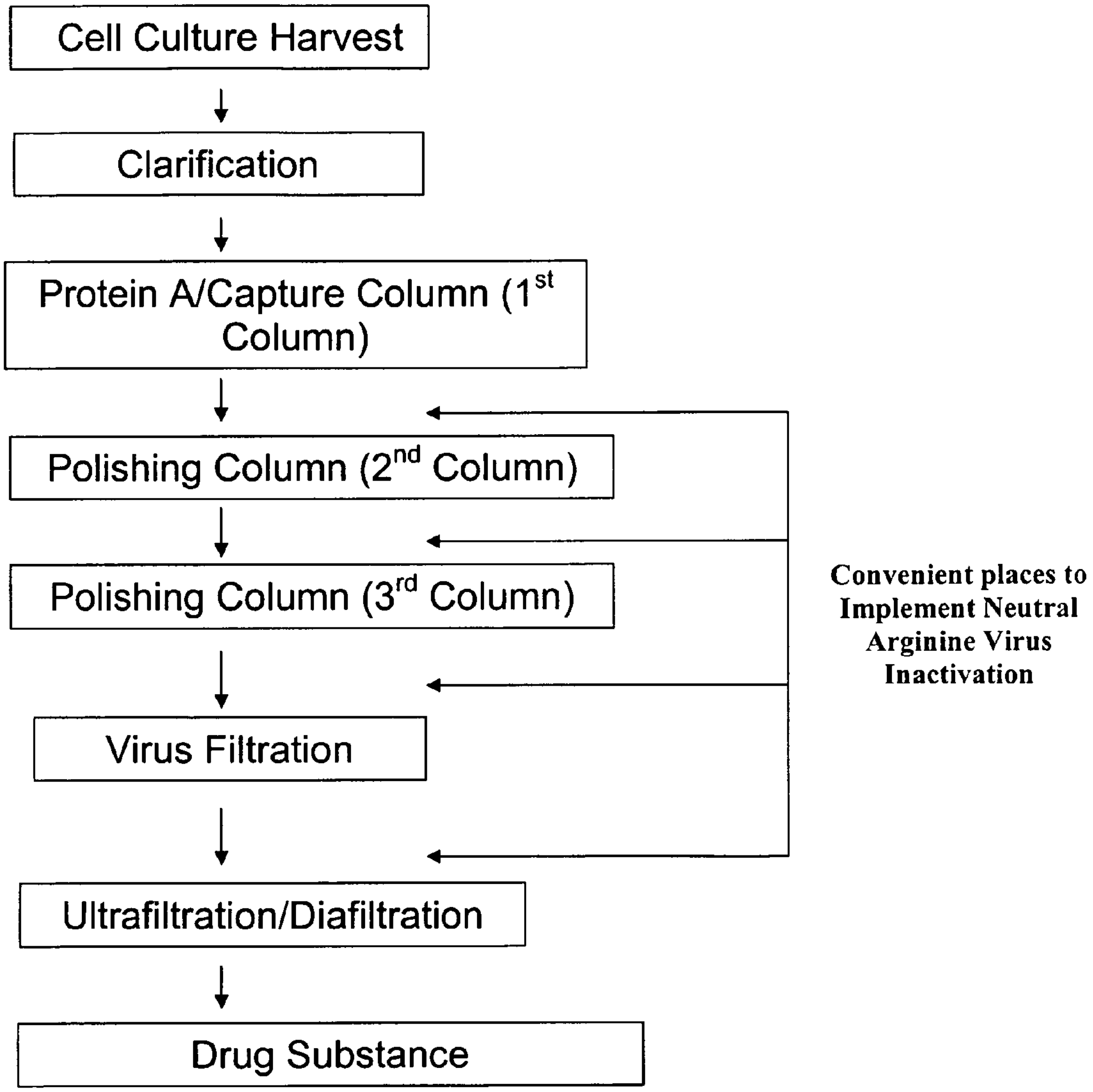
FIG. 13 depicts a process flow chart for purification of proteins and arginine inactivation of viruses.

X-MLV was not inactivated in the presence of 1.0M glycine (Table 22, FIG. 12). The results showed that high concentrations of glycine were not effective for inactivating enveloped viruses (such as X-MLV).

TABLE 22

| X-MLV in Glycine Buffer Inactivation Studies | | | | |
|---|---|---|---|---|
| Sample ID/ Description | Titer of quenched sample, $Log_{10}$ $TCID_{50}/mL^a$ | Dilution factor from quench[b] | Adjusted titer of sample, $Log_{10}$ $TCID_{50}/mL^c$ | RF[d] |
| Run 9 | | | | |
| Virus Control | 5.13 | N/A[e] | 5.13 | N/A |
| Load Control | 4.38 | 10 | 5.38 | N/A |
| Hold Control | 4.75 | 10 | 5.75 | −0.37 |
| Time = 15 | 5.00 | 10 | 6.00 | −0.62 |
| Time = 30 | 5.00 | 10 | 6.00 | −0.62 |
| Time = 60 | 4.50 | 10 | 5.50 | −0.12 |
| Time = 120 | 4.50 | 10 | 5.50 | −0.12 |
| Time = 240 (quenched) | 4.63 | 10 | 5.63 | −0.25 |
| Time = 240 (non-quenched)* | 5.60 | 1 | 5.60 | −0.22 |
| Run 10 | | | | |
| Load Control | 4.13 | 10 | 5.13 | N/A |
| Hold Control | 4.25 | 10 | 5.25 | −0.12 |
| Time = 15 | 4.50 | 10 | 5.50 | −0.37 |
| Time = 30 | 4.38 | 10 | 5.38 | −0.25 |
| Time = 60 | 4.38 | 10 | 5.38 | −0.25 |
| Time = 120 | 4.63 | 10 | 5.63 | −0.50 |
| Time = 240 (quenched) | 4.88 | 10 | 5.88 | −0.75 |
| Time = 240 (non-quenched)* | 5.60 | 1 | 5.60 | −0.47 |

[a]Titer obtained from $TCID_{50}$ assay.

[b]Dilution factor = 10 (from quenching 1 mL of spiked TA with 9 mL of media).

[c]Titer of sample, adjusted for the dilution factor. Obtained by multiplying titer from $TCID_{50}$ assay and the dilution factor from the quench, if appropriate.

$$^dRF = \log_{10}\frac{(\text{Input virus titer per mL})}{(\text{Ouput virus titer per mL})}$$

Note:

Input volume = output volume.

[e]Not applicable; there is no quench for this sample so dilution factor is 1.

The study showed buffers containing high arginine concentrations (at neutral pH) possess a unique property that effectively inactivates enveloped viruses, such as X-MLV and SuHV-1. Glycine was not effective for virus inactivation.

Table 23 summarizes the results of the studies, including virus inactivation (Reduction Factor). The enveloped viruses evaluated in the studies (X-MLV and SuHV-1) were inactivated in the presence of 1.0M arginine, while the non-enveloped virus (MMV) was not inactivated. Use of 1.0M glycine did not inactivate X-MLV. The results show use of high concentrations of arginine (1.0M) in a neutral buffer could be useful as an effective virus inactivation method for enveloped viruses.

TABLE 23

Summary of Virus clearance for the Neutral Amino Acid Buffer Inactivation Studies

| Run number | Buffer Description | Virus | Input virus titer, $log_{10}$ $TCID_{50}$/mL | Output virus titer, $log_{10}$ $TCID_{50}$/mL[a] | Virus inactivation, RF[b] |
|---|---|---|---|---|---|
| 11 | 5 mM Tris + 0.1M | X-MLV | 5.63 | 5.29 | 0.3 |
| 12 | Arginine (pH 7.0) | | 5.88 | 5.53 | 0.3 |
| 13 | 5 mM Tris + 0.5M | X-MLV | 5.75 | 2.37 | 3.4 |
| 14 | Arginine (pH 7.0) | | 5.63 | 2.13 | 3.5 |
| 1 | 5 mM Tris + 1.0M | SuHV-1 | 5.25 | ≤1.57 | ≥3.68 |
| 2 | Arginine (pH 7.0) | | 5.00 | ≤1.57 | ≥3.43 |
| 3 | 5 mM Tris + 1.0M | MMV | 7.13 | 7.38 | −0.25 |
| 4 | Arginine (pH 7.0) | | 7.50 | 7.75 | −0.25 |
| 5 | 50 mM Histidine + | X-MLV | 4.33 | ≤2.53 | ≥1.80 |
| 6 | 50 mM CaCl2 + 1.0M Arginine + 0.04% Tween-80 + 50% Propylene Glycol (pH 7.0) | | 4.58 | ≤2.53 | ≥2.05 |
| 7 | 50 mM Histidine + | SuHV-1 | 4.60[c] | ≤2.05 | ≥2.55 |
| 8 | 50 mM CaCl2 + 1.0M Arginine + 0.04% Tween-80 + 50% Propylene Glycol (pH 7.0) | | 4.48[c] | ≤2.05 | ≥2.43 |
| 9 | 5 mM Tris + 1.0M | X-MLV | 5.38 | 5.63 | −0.25 |
| 10 | Glycine (pH 7.0) | | 5.13 | 5.88 | −0.75 |

[a]Output Virus titer represents the last time point (120 or 240 minutes) for each study

[b]Calculation:

$$RF = Log_{10}\frac{(\text{Input virus titer per mL}) \times \text{Input volume}}{(\text{Output virus titer per mL}) \times \text{Output volume}}$$

[c]The Load control was used as the input for these runs, since the Hold control was completely inactivated.

Example 3

Effect of Arginine Virus Inactivation on Product Quality

To examine the effect of arginine virus inactivation on the product quality of therapeutic biological products, four protein products were incubated with a high concentration of arginine. The protein products were obtained as final process intermediates and incubated for 24 hours at either a low pH of 3.7 or an arginine concentration of 1.0 M by bolus addition. Protein product aggregation was determined by size exclusion chromatography. The results are shown in Table 24.

TABLE 24

Aggregate Formation of Therapeutic Biological Products Incubated at Low pH or High Arginine Concentration Measured as % Monomer

| Protein Examined | % Monomer T = 0 hr | % Monomer T = 24 hr | | |
|---|---|---|---|---|
| (Protein type) | Control | Control | Low pH | Arginine |
| FIX (Fusion protein) | 99.6 | 99.2 | 50.2 | 92.9 |
| Lingo (mAb) | 99.8 | 99.8 | 27.0 | 99.1 |
| GE2 (Fusion protein) | 97.1 | 97.2 | 73.0 | 98.4 |
| TWEAK (mAb) | 99.3 | 99.2 | 99.3 | 99.0 |

Figure 14:
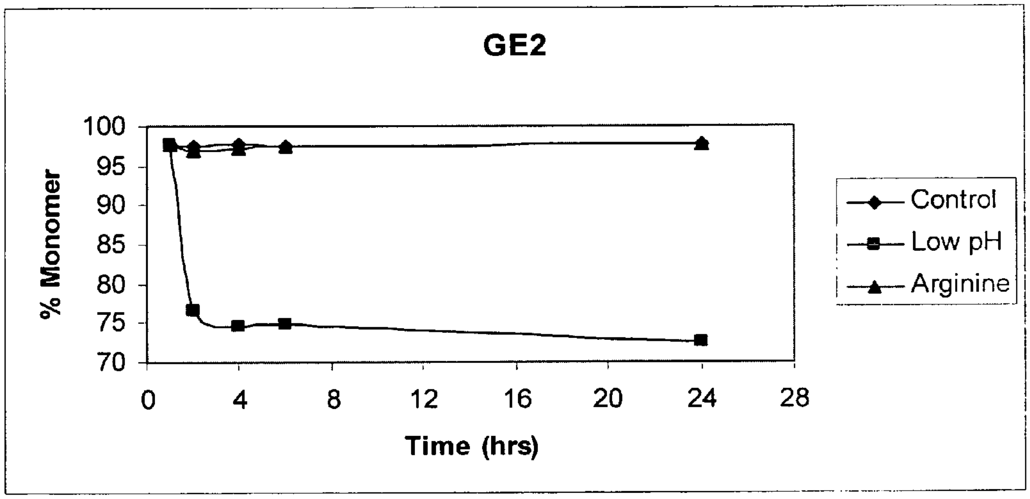
FIG. 14 depicts percentage of GE2 protein monomer remaining over a 24-hour incubation period at low pH (3.7) or high arginine concentration (1.0 M) as compared to a control solution.
Figure 15:
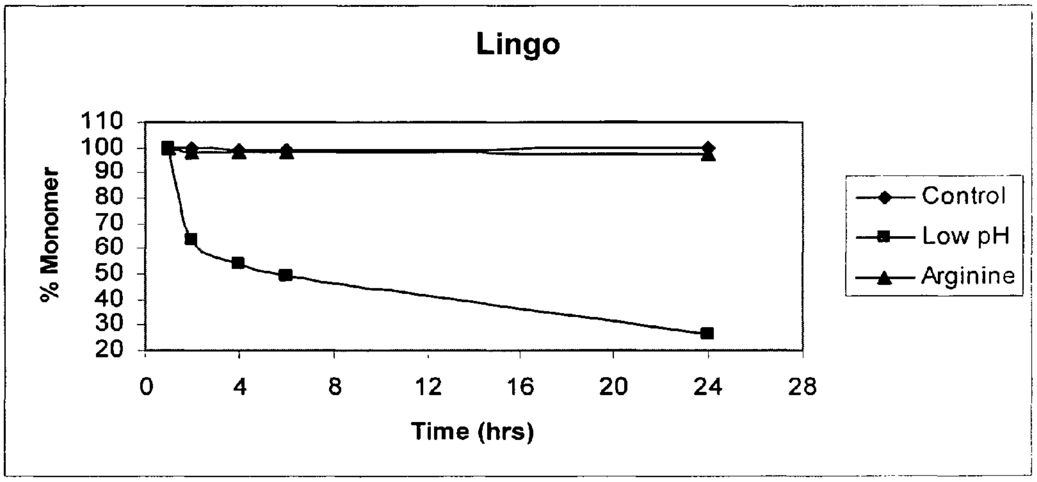
FIG. 15 depicts percentage of Lingo protein monomer remaining over a 24-hour incubation period at low pH (3.7) or high arginine concentration (1.0 M) as compared to a control solution.
Figure 16:
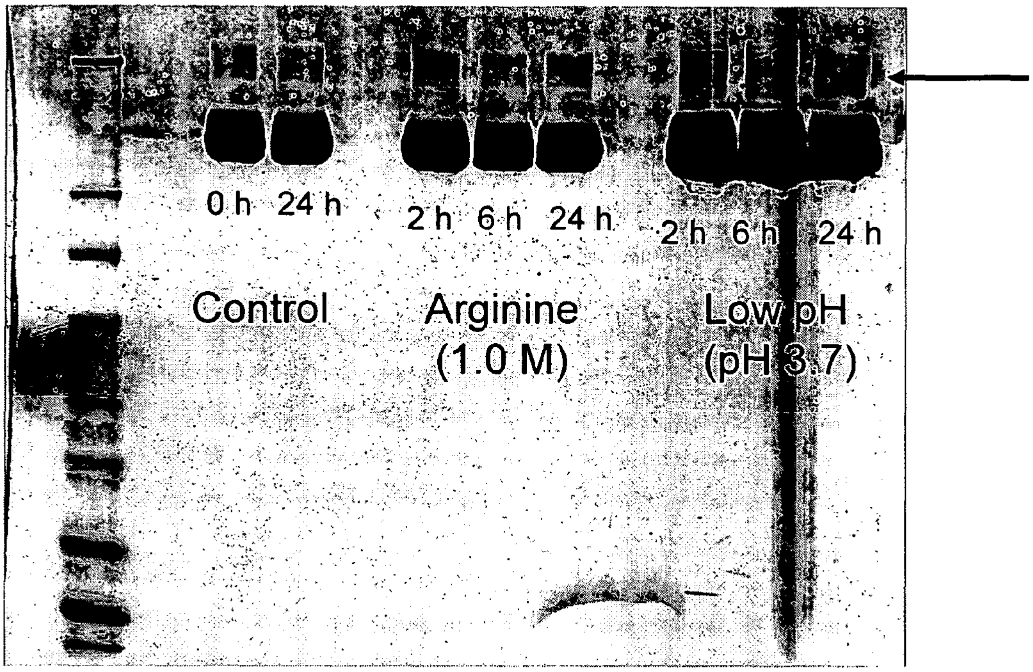
FIG. 16 depicts high-molecular weight protein aggregation over a 24-hour incubation period of GE2 protein at low pH (3.7) or high arginine concentration (1.0 M) as compared to a control solution. The arrow points to formation of high-molecular weight species.

Aggregate levels for protein products Lingo, GE2 and TWEAK were the same or better than the control after incubation in 1.0 M arginine for 24 hours. The percentage of FIX monomer remaining after 24 hours of incubation in 1.0 M arginine was only slightly lower than control (see Table 24). However, unlike incubation in 1.0 M arginine, the stability of the protein products after 24 hours at pH 3.7 was quite variable. Only TWEAK demonstrated a high percentage of protein monomer remaining after 24 hours, while GE2, FIX, and Lingo showed a considerable amount of protein aggregation (see Table 24 and FIGS. 14 and 15 for GE2 and Lingo, respectively). The presence of high-molecular weight species in the protein product samples incubated at low pH was confirmed by SDS-PAGE gel analysis (see FIG. 16 for GE2, arrow shows increased amount of high-molecular weight species).

These product quality studies demonstrate that high concentrations of arginine have little to no detrimental effect on product quality, and thus, provide potential flexibility for manufacturing. Similar protein aggregation trends were observed when the protein concentration was 1/10 the concentration of the initial studies (data not shown). Therefore, protein concentration did not affect aggregate species formation when the protein product was exposed to high concentrations of arginine. However, the rate of arginine addition to the sample did appear to have an effect on the formation of aggregate species.

Figure 17:
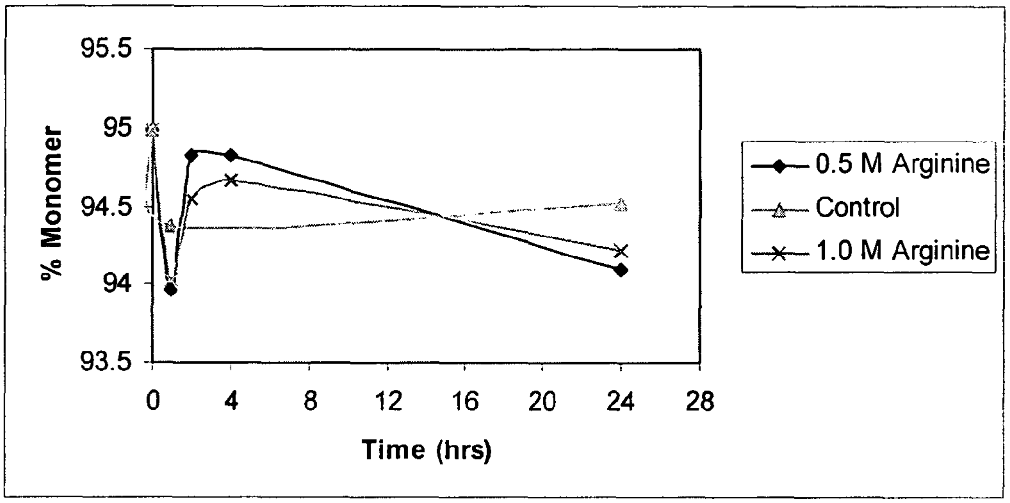
FIG. 17 depicts percentage of FIX protein monomer remaining over a 24-hour incubation period following bolus addition of arginine to a final concentration of 0.5 M or 1.0 M compared to a controlled drop-wise addition of arginine.

For example, a bolus addition of the arginine stock solution results in localized higher concentrations in the sample resulting in some aggregate formation. However, drop-wise addition of the arginine stock solution (drop-wise addition of 1 mL arginine stock solution to reach final arginine concentration after 5 minutes) mitigates aggregate formation, although some initial aggregation still occurs (see FIG. 17 which shows the stability of a FIX fusion protein). Because the rate of arginine stock solution can be readily controlled in the manufacturing environment, the use of high concentrations of arginine to inactivate or reduce the infectious titer of viruses serves as an effective alternative to current practices that use harsh conditions such as low pH.

As demonstrated in this Example, therapeutic proteins such as fusion proteins and monoclonal antibodies show good product stability in the presence of high concentrations of arginine. Thus, in some embodiments, methods of inactivating or reducing the infectious titer of a virus comprising contacting the virus with arginine are applied during isolation and/or production of therapeutic proteins. Some examples of such therapeutic proteins include, without limitation, fusion proteins such as Factor IX-Fc (FIX-Fc), as shown above, and additional Fc-fusion proteins such as clotting factor, Factor VII, and Factor VIII-Fc fusion proteins and others, for example, such as those disclosed in U.S. Pat. Nos. 7,348,004; 7,381,408; and 7,404,956 and U.S. Patent Appl. Publ. No. US 2005/0147618 A1, each of which are incorporated by reference herein. Therapeutic proteins also include, without limitation, antibodies such as antibodies that bind LINGO-1 or antibodies that bind TWEAK receptor (Fn14), which are disclosed in International Appl. Publ. Nos. WO 2007/008547 and WO 2008/086006 and International Appl. No. PCT/US2009/003999, for Lingo antibodies, or International Appl. No. PCT/US2009/043382 for TWEAK receptor antibodies, each of which are incorporated by reference herein.

Embodiments of the Invention (E) Include E1-E31:

E1. A method of inactivating or reducing the infectious titer of an enveloped virus comprising contacting said virus with arginine, wherein said contacting occurs in a solution comprising at least about 0.2 M arginine and wherein said solution is at a pH above about 6.0.

E2. A method of inactivating or reducing the infectious titer of an enveloped virus contaminating a therapeutic biological product comprising contacting said virus with arginine, wherein said contacting occurs in a solution comprising at least about 0.2 M arginine and wherein said solution is at a pH above about 6.0.

E3. The method of E1 or E2, wherein said pH is selected from the group consisting of:

a) pH of about 6.0 to about 8.5;
b) pH of about 6.5 to about 8.0;
c) pH of about 6.5 to about 7.5;
d) pH of about 6.0 to 8.0;
e) pH of about 7.0 to about 8.0;
f) pH of about 7.0 to about 7.5;
g) pH of about 6.0;
h) pH of about 6.5;
i) pH of about 7.0;
j) pH of about 7.5;
k) pH of about 8.0; and,
l) pH of about 8.5.

E4. The method of any one of E1 to E3, wherein said concentration of arginine is selected from the group consisting of:

a) about 0.3 M;
b) about 0.4 M;
c) about 0.5 M;
d) about 0.6 M;
e) about 0.7 M;
f) about 0.8 M;
g) about 0.9 M;
h) about 1.0 M;
i) about 1.1 M;
j) about 1.2 M;
k) about 1.3 M;
l) about 1.4 M;
m) about 1.5 M;
n) about 1.6 M;
o) about 1.7 M;
p) about 1.8 M;
q) about 1.9 M;
r) about 2.0 M;
s) about 2.1 M;
t) about 2.2 M;
u) about 2.3 M;
v) about 2.4 M;
w) about 2.5 M;
x) about 3 M;
y) about 3.5 M;
z) about 4 M;
aa) about 4.5M;
ab) about 5 M;
ac) about 5.5 M;
ad) about 6 M;
ad) about 6.5 M;
ad) about 7 M; and
ae) about 7.5M.

E5. The method of any one of E1 to E4, wherein said virus is contacted with said solution further comprising a glycol compound.

E6. The method of E5, wherein said glycol compound is present at a concentration of less than or equal to about 50% (weight to volume).

E7. The method of E5 or E6, wherein said glycol compound is selected from the group consisting of:

a) propylene glycol;
b) polypropylene glycol;
c) ethylene glycol;
d) polyethylene glycol;
e) hexylene glycol; and,
f) polyhexylene glycol.

E8. The method of any one of E1 to E7, wherein said inactivating or reducing is performed as part of a product purification process.

E9. The method of E8, wherein said inactivating or reducing is performed during a cell culture harvest procedure.

E10. The method of E8, wherein said inactivating or reducing is performed during a cell culture clarification procedure.

E11. The method of E8, wherein said inactivating or reducing is performed prior to a chromatography purification procedure, wherein said procedure comprises contacting said therapeutic biological product with a chromatographic media.

E12. The method of E8, wherein said inactivating or reducing is performed subsequent to a chromatography purification procedure, wherein said procedure comprises contacting said therapeutic biological product with a chromatographic media.

E13. The method of E8, wherein said inactivating or reducing is performed subsequent to one or more chromatography purification procedures but prior to another or more chromatography purification procedures, wherein said procedures comprise contacting said therapeutic biological product with a chromatographic media.

E14. The method of E8, wherein said inactivating or reducing is performed subsequent to all chromatography purification procedures used in preparing said biological product.

E15. The method of E8, wherein said inactivating or reducing is performed prior to a virus filtration procedure.

E16. The method of E8, wherein said inactivating or reducing is performed subsequent to a virus filtration procedure.

E17. The method of E8, wherein said inactivating or reducing is performed subsequent to a virus filtration procedure and prior to an ultrafiltration or diafiltration procedure.

E18. The method of E8, wherein said inactivating or reducing is performed prior to an ultrafiltration or diafiltration procedure.

E19. The method of E8, wherein said inactivating or reducing is performed subsequent to an ultrafiltration or diafiltration procedure.

E20. The method of any one of E1 to E19, wherein the therapeutic biological product comprises a recombinant protein.

E21. The method of any one of E1 to E19, wherein said therapeutic biological product comprises a naturally occurring or recombinant immunoglobulin.

E22. The method of any one of E1 to E19, wherein said therapeutic biological product comprises a naturally occurring or recombinant blood coagulation factor.

E23. The method of claim E22, wherein said blood coagulation factor is selected from the group consisting of:

a) fibrinogen (Factor I);
b) fibrin;
c) prothrombin (Factor II);
d) thrombin;
e) anti-thrombin;
f) Tissue factor Co-factor of VIIa (Factor III);
g) Protein C;
h) Protein S;
i) protein Z;
j) Protein Z-related protease inhibitor;
k) heparin cofactor II;
l) Factor V (proaccelerin, labile factor);
m) Factor-VH;
n) Factor-VIII;
o) Factor-IX;
p) Factor-X;
q) Factor-XI;
r) Factor-XII;
s) Factor-XIII;
t) von Willebrand factor;
u) prekallikrein;
v) high molecular weight kininogen;
w) plasminogen;
x) plasmin;
y) tissue-plasminogen activator;
z) urokinase;
aa) plasminogen activator inhibitor-1; and,
ab) plasminogen activator inhibitor-2.

E24. The method of any one of E1 to E22, wherein said biological product is produced by eukaryotic cells.

E25. The method of E24, wherein said biological product is produced by mammalian cells.

E26. The method of E25, wherein said biological product is produced by Chinese Hamster Ovary (CHO) cells.

E27. The method of E25, wherein said biological product is produced by NSO murine myeloma cells.

E28. The method of E25, wherein said biological product is produced by human cells.

E29. The method of any one of E1 to E28, wherein said therapeutic protein is a fusion protein.

E30. The method of E29, wherein said fusion protein is an Fc-fusion protein.

E31. The method of E21, wherein said naturally occurring or recombinant immunoglobulin is an antibody that binds LINGO-1 or an antibody that binds TWEAK receptor (Fn14).

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method of inactivating or reducing the infectious titer of a retrovirus comprising contacting said virus with arginine, wherein said contacting occurs in a solution comprising at least about 0.2 M arginine and wherein said solution is at a pH above about 6.0.

2. The method of claim 1, wherein said retrovirus contaminates a therapeutic biological product.

3. The method of claim 1, wherein said pH is selected from the group consisting of a) pH of about 6.0 to about 8.5;
b) pH of about 6.5 to about 8.0;
c) pH of about 6.5 to about 7.5;
d) pH of about 6.0 to 8.0;
e) pH of about 7.0 to about 8.0;
f) pH of about 7.0 to about 7.5;
g) pH of about 6.0;
h) of about 6.5;
i) pH of about 7.0;
j) pH of about 7.5;
k) pH of about 8.0; and,
l) pH of about 8.5.

4. The method of claim 1, wherein said concentration arginine is selected from the group consisting of:

a) about 0.3 M;
b) about 0.4 M;
c) about 0.5 M;
d) about 0.6 M;
e) about 0.7 M;
f) about 0.8 M;
g) about 0.9 M;
h) about 1.0 M;
i) about 1.1 M;
j) about 1.2 M;
k) about 1.3 M;
l) about 1.4 M;
m) about 1.5 M;
n) about 1.6 M;
o) about 1.7 M;
p) about 1.8 M;
q) about 1.9 M;
r) about 2.0 M;
s) about 2.1 M;
t) about 2.2 M;
u) about 2.3 M;
v) about 2.4 M;
w) about 2.5 M;
x) about 3 M;
y) about 3.5 M;
z) about 4 M;
aa) about 4.5 M;
ab) about 5 M;
ac) about 5.5 M;
ad) about 6 M;
ad) about 6.5 M;
ad) about 7 M; and
ae) about 7.5 M.

5. The method of claim 1, wherein said retrovirus is contacted with said solution that further comprises a glycol compound.

6. The method of claim 5, wherein said glycol compound is present at a concentration of less than or equal to about 50% (weight to volume).

7. The method of claim 5, wherein said glycol compound is selected from the group consisting of:

a) propylene glycol;
b) polypropylene glycol;
c) ethylene glycol;
d) polyethylene glycol;
e) hexylene glycol; and,
f) polyhexylene glycol.

8. The method of claim 1, wherein said inactivating or reducing is performed as part of a product purification process.

9. The method of claim 8, wherein said inactivating or reducing is performed during a cell culture harvest procedure.

10. The method of claim 8, wherein said inactivating or reducing is performed during a cell culture clarification procedure.

11. The method of claim 2, wherein said inactivating or reducing is performed prior to a chromatography purification procedure, wherein said chromatography purification procedure comprises contacting said retrovirus contaminated therapeutic biological product with a chromatographic media.

12. The method of claim 2, wherein said inactivating or reducing is performed subsequent to a chromatography purification procedure, wherein said chromatography purification procedure comprises contacting said retrovirus contaminated therapeutic biological product with a chromatographic media.

13. The method of claim 2, wherein said inactivating or reducing is performed subsequent to one or more chromatography purification procedures but prior to another or more chromatography purification procedures, wherein said chromatography purification procedures comprise contacting said retrovirus contaminated therapeutic biological product with a chromatographic media.

14. The method of claim 2, wherein said inactivating or reducing is performed subsequent to all chromatography purification procedures used in preparing said retrovirus contaminated therapeutic biological product.

15. The method of claim 8, wherein said inactivating or reducing is performed prior to a virus filtration procedure.

16. The method of claim 8, wherein said inactivating or reducing is performed subsequent to a virus filtration procedure.

17. The method of claim 8, wherein said inactivating or reducing is performed subsequent to a virus filtration procedure and prior to an ultrafiltration or diafiltration procedure.

18. The method of claim 8, wherein said inactivating or reducing is performed prior to an ultrafiltration or diafiltration procedure.

19. The method of claim 8, wherein said inactivating or reducing is performed subsequent to an ultrafiltration or diafiltration procedure.

20. The method of claim 2, wherein the therapeutic biological product comprises a recombinant protein.

21. The method of claim 2, wherein said therapeutic biological product comprises a naturally occurring or recombinant immunoglobulin.

22. The method of claim 2, wherein said therapeutic biological product comprises a naturally occurring or recombinant blood coagulation factor.

23. The method of claim 22, wherein said blood coagulation factor is selected from the group consisting of:

a) fibrinogen (Factor I);
b) fibrin;
c) prothrombin (Factor II);
d) thrombin;
e) anti-thrombin;
f) Tissue factor Co-factor of VIIa (Factor III);
g) Protein C;
h) Protein S;
i) protein Z;
j) Protein Z-related protease inhibitor;
k) heparin cofactor II;
l) Factor V;
m) Factor-VII;
n) Factor-VIII;
o) Factor-IX;
p) Factor-X;
q) Factor-XI;
r) Factor-XII;
s) Factor-XIII;
t) von Willebrand factor;
u) prekallikrein;
v) high molecular weight kininogen;
w) plasminogen;
x) plasmin;
y) tissue-plasminogen activator;
z) urokinase;
aa) plasminogen activator inhibitor-1; and
ab) plasminogen activator inhibitor-2.

24. The method of claim 2, wherein said therapeutic biological product is produced by eukaryotic.

25. The method of claim 24, wherein said eukaryotic cells are mammalian cells.

26. The method of claim 25, wherein said mammalian cells are Chinese Hamster Ovary (CHO) cells.

27. The method of claim 25, wherein said mammalian cells are NSO murine myeloma cells.

28. The method of claim 25, wherein said mammalian cells are human cells.

29. The method of claim 1, wherein the concentration of arginine is gradually increased using a step-wise or continuous gradient to a final concentration of at least about 0.2 M arginine.

30. The method of claim 29, wherein said final concentration of arginine is increased by the step-wise or continuous gradient at a rate of about 20% or less per minute.

31. The method of claim 3, wherein said pH is about 6.5 to 7.5.

32. The method of claim 3, wherein said pH is about 7.0.

33. The method of claim 1, wherein said concentration of arginine is about 0.5 M to 3.0 M.

34. The method of claim 4, wherein said concentration of arginine is about 1.0 M.

35. The method of claim 7, wherein said glycol compound is propylene glycol.

* * * * *